(12) United States Patent
Wolff et al.

(10) Patent No.: US 6,706,922 B2
(45) Date of Patent: Mar. 16, 2004

(54) PROCESS OF MAKING A COMPOUND BY FORMING A POLYMER FROM A TEMPLATE DRUG

(75) Inventors: Jon A. Wolff, Madison, WI (US); James E. Hagstrom, Madison, WI (US); Vladimir G. Budker, Madison, WI (US); Vladimir S. Trubetskoy, Madison, WI (US); Paul M. Slattum, Madison, WI (US); Lisa J. Hanson, Madison, WI (US)

(73) Assignee: Mirus Corporation, Madison, WI (US)

( * ) Notice: Subject to any disclaimer, the term of this patent is extended or adjusted under 35 U.S.C. 154(b) by 128 days.

(21) Appl. No.: 09/993,216

(22) Filed: Nov. 16, 2001

(65) Prior Publication Data

US 2002/0165184 A1 Nov. 7, 2002

Related U.S. Application Data

(60) Division of application No. 09/000,692, filed on Dec. 30, 1997, now Pat. No. 6,339,067, which is a continuation-in-part of application No. 08/778,657, filed on Jan. 3, 1997, now Pat. No. 6,126,964.

(51) Int. Cl.$^7$ .................. C07C 211/63; C07C 211/09; C07C 211/13
(52) U.S. Cl. ................. 564/295; 560/158; 560/169
(58) Field of Search ................ 560/158, 169; 564/295

(56) References Cited

U.S. PATENT DOCUMENTS 5,264,618 A * 11/1993 Felgner et al. .............. 560/224

* cited by examiner

Primary Examiner—Brian Davis
(74) Attorney, Agent, or Firm—Mark K Johnson

(57) ABSTRACT

A method of forming polymers in the presence of nucleic acid using template polymerization. Also, a method of having the polymerization occur in heterophase systems. These methods can be used for the delivery of nucleic acids, for condensing the nucleic acid, for forming nucleic acid binding polymers, for forming supramolecular complexes containing nucleic acid and polymer, and for forming an interpolyelectrolyte complex.

3 Claims, 6 Drawing Sheets

PROCESS OF MAKING A COMPOUND BY FORMING A POLYMER FROM A TEMPLATE DRUG

CROSS-REFERENCE TO RELATED APPLICATIONS

This is a divisional of 09/000,692 filed Dec. 30, 1997 now U.S. Pat. No. 6,339,067, which is a continuation-in-part of application: application Ser. No. 08/778,657 filing date Jan. 3, 1997 now U.S. Pat. No. 6,126,964.

FEDERALLY SPONSORED RESEARCH not applicable

BACKGROUND

Polymers are used for drug delivery for a variety of therapeutic purposes. Polymers have also been used for the delivery of nucleic acids (polynucleotides and oligonucleotides) to cells for therapeutic purposes that have been termed gene therapy or anti-sense therapy. One of the several methods of nucleic acid delivery to the cells is the use of DNA-polycations complexes. It was shown that cationic proteins like histones and protamines or synthetic polymers like polylysine, polyarginine, polyomithine, DEAE dextran, polybrene, and polyethylenimine were effective intracellular delivery agents while small polycations like spermine were ineffective. (Felgner, P. L. (1990) Advanced Drug Delivery Rev. 5, 163–187; Boussif, O., Lezoualch, F., Zanta, M. A., Mergny, M. D., Scherman, D., Demeneix, B., & Behr, J. P. (1995) Proc. Natl. Acad. Sci. USA 92, 7297–7301) The mechanism by which polycations facilitate uptake of DNA is not completely understood but the following are some important principles:

1) Polycations Provide Attachment of DNA to the Target Cell Surface:

The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a very convenient linker for attaching specific receptors to DNA and as result, DNA-polycation complexes can be targeted to specific cell types.(Perales, J. C., Ferkol, T. Molas, M. & Hanson, W. (1994) Eur. J. Biochem. 226, 255–266; Cotten, M., Wagner, E. & Birustiel, M. L. (1993) Methods in Enzymology 217, 618–644; Wagner, E., Curiel, D., & Cotten, M. (1994) Advanced Drug Delivery Rev. 114, 113–135).

2) Polycations Protect DNA in Complexes Against Nuclease Degradation (Chiou, H. C., Tangco, M. V. Levine, S. M., Robertson, D., Kormis, K., Wu, C. H., & Wu, G. Y. (1994) Nucleic Acids Res. 22, 5439–5446). This is important for both extra- and intracellular preservation of DNA. The endocytic step in the intracellular uptake of DNA-polycation complexes is suggested by results in which DNA expression is only obtained by incorporating a mild hypertonic lysis step (either glycerol or DMSO) (Lopata, M. A., D. Clevland, W., & Sollner-Webb, B. (1984) Nucleic Acids Res. 12, 5707–5717; Golub, E.I., Kim, H. & Volsky, D. J. (1989) Nucleic Acid Res. 17, 4902). Gene expression is also enabled or increased by preventing endosome acidification with $NH_4Cl$ or chloroquine (Luthman, H. & Magnusson, G. (1983) Nucleic Acids Res. 11, 1295–1300). Polyethylenimine which facilitates gene expression without additional treatments probably disrupts endosomal function itself (Boussif, O., Lezoualch, F., Zanta, M. A., Mergny, M.D., Scherman, D., Demeneix, B., & Behr, J.P. (1995) Proc. Natl. Acad. Sci. USA 92, 7297–7301). Disruption of endosomal function has also been accomplished by linking to the polycation endosomal-disruptive agents such as fusion peptides or adenoviruses (Zauner, W., Blaas, D., Kuechler, E., Wagner, E., (1995) J. Virology 69, 1085–1092; Wagner, E., Plank, C., Zatloukal, K., Cotten, M., & Birmstiel, M. L. (1992) Proc. Natl. Acad. Sci. 89, 7934–7938) (Fisher, K. J., & Wilson, J. M. (1994) Biochemical J. 299, 49–58).

3) Polycations Generate DNA Condensation:

The volume which one DNA molecule occupies in complex with polycations is drastically lower than the volume of a free DNA molecule. The size of DNA/polymer complex is critical for gene delivery in vivo. In terms of intravenous injection, DNA needs to cross the endothelial barrier and reach the parenchymal cells of interest. The largest endothelia fenestrae (holes in the endothelial barrier) occurs in the liver and have an average diameter 100 mn. The fenestrae size in other organs is much lower. The size of the DNA complexes is also important for the cellular uptake process. After binding to the target cells the DNA-polycation complex should be taken up by endocytosis. Since the endocytic vesicles have a homogenous internal diameter of about 100 nm in hepatocytes of similar size in other cell types, the DNA complexes need to be smaller than 100 nm (Geuzze, H. J., Slot, J. W., Strous, G. J., Lodish, H. F., & Schwartz, A. L. (1982) J. Cell Biol. 92, 865–870).

Condensation of DNA

A significant number of multivalent cations with widely different molecular structures have been shown to induce the condensation of DNA. These include spermidine, spermine, $Co(NH_3)_63+$, protamine, histone Hi, and polylysine. (Gosule, L. C. & Schellman, J. A. (1976) Nature 259, 333–335; Chattoraj, D. K., Gosule, L. C. & Schellman, J. A. (1978) J. Mol. Biol. 121, 327–337; Had, N. V., Downing, K. H. & Balhorn, R. (1993) Biochem. Biophys. Res. Commun. 193, 1347–1354; Hsiang, M. W & Cole, R. D. (1977) Proc. Natl. Acad. Sci. USA 74, 4852–4856; Haynes, M., Garret, R. A. & Gratzer, W. B. (1970) Biochemistry 9, 4410–4416; Widom, J. & Baldwin, R. L. (1980) J. Mol. Biol. 144, 431–453.). Quantitative analysis has shown DNA condensation to be favored when 90% or more of the charges along the sugar-phosphate backbone are neutralized (Wilson, R. W. & Bloomfield, V. A. (1979) Biochemistry 18, 2192–2196). Depending upon the concentration of the DNA condensation leads to three main types of structures:

1) In extremely dilute solution (about 1 ug/ml or below), long DNA molecules can undergo a monomolecular collapse and form structures described as toroid.

2) In very dilute solution (about 10 ug/ml) microaggregates form with short or long molecules and remain in suspension. Toroids, rods and small aggregates can be seen in such solution.

3) In dilute solution (about 1 mg/ml, large aggregates are formed that sediment readily. (Sicorav, J. -L., Pelta, J., & Livolant, F (1994) Biophysical Journal 67, 1387–1392).

Toroids have been considered an attractive form for gene delivery because they have the lowest size. While the size of DNA toroids produced within single preparations has been shown to vary considerably, toroid size is unaffected by the length of DNA being condensed. DNA molecules from 400 bp to genomic length produce toroids similar in size (Bloomfield, V. A. (1991) Biopolymers 31, 1471–1481). Therefore one toroid can include from one to several DNA molecules. The kinetics of DNA collapse by polycations which resulted in toroids is very slow. For example DNA condensation by Co(NH3)6Cl3 needs 2 hours at room temperature.(Arscott, P. G., Ma, C., & Bloomfield, V. A. (1995) Biopolymers 36, 345–364).

The mechanism of DNA condensation is not obvious. The electrostatic forces between unperturbed helices arise primarily from a counterion fluctuation mechanism requiring multivalent cations and plays the major role in DNA condensation.(Riemer, S. C. & Bloomfield, V. A. (1978) Biopolymers 17, 789–794; Marquet, R. & Houssier, C. (1991) J. Biomol. Struct. Dynam. 9, 159–167; Nilsson, L. G., Guldbrand, L. & Nordenskjold L. (1991) Mol. Phys. 72, 177–192). The hydration forces predominate over electrostatic forces when the DNA helices approach closer then a few water diameters (Leikin, S., Parsegian, V. A., Rau, D.C. & Rand, R. P. (1993) Ann. Rev. Phys. Chem. 44, 369–395). In case of DNA-polymeric polycation interactions, DNA condensation is a more complicated process than the case of low molecular weight polycations. Different polycationic proteins can generate toroid and rod formation with different size DNA at a ratio of positive to negative charge of 0.4 (Garciaramirez, M., & Subirana, J. A. (1994) Biopolymers 34, 285–292). It was shown by fluorescence microscopy that T4 DNA complexed with polyarginine or histone can forms two types of structures; an elongated structure with a long axis length of about 350 mn (like free DNA) and dense spherical particles.(Minagawa, K., Matsuzawa, Y., Yshikawa, K., Matsumoto, M., & Doi, M. (1991) FEBS Lett. 295, 60–67). Both forms exist simultaneously in the same solution. The reason for the co-existence of the two forms can be explained as an uneven distribution of the polycation chains among the DNA molecules. The uneven distribution generates two thermodynamically favorable conformations. (Kabanov, A. V., & Kabanov, V. A. (1995) Bioconjugate Chem. 6, 7–20).

It was also shown that the electrophoretic mobility of DNA -polycation complexes can change from negative to positive in excess of polycation. It is likely that large polycations don't completely align along DNA but form polymer loops which interact with other DNA molecules. The rapid aggregation and strong intermolecular forces between different DNA molecules may prevent the slow adjustment between helices needed to form tightly packed, orderly particles. This specification describes a new approach, that we have termed Polynucleotide Template Polymerization, for overcoming this problem of nonspecific aggregation and large DNA-polycation complex formation that occurs when polycation/DNA complexes are formed in DNA concentrations that are of practical value for polynucleotide transfer into cells and for gene or antisense therapy.

SUMMARY OF INVENTION

A process for drug delivery is described in which polymerization and chemical reaction processes are induced in the presence of the drug in order to deliver the drug or biologically active compound. Drug delivery encompasses the delivery of a biologically active compound to a cell. By "delivering" we mean that the drug becomes associated with the cell. The drug can be on the membrane of the cell or inside the cytoplasm, nucleus, or other organelle of the cell. The process of delivering a polynucleotide to a cell has also been commonly termed "transfection" or the process of "transfecting" and also it has been termed "transformation".

A biologically active compound is a compound having the potential to react with biological components. Pharmaceuticals, proteins, peptides and nucleic acids are examples of biologically active compounds. The template polymer can be a polyanion such as a nucleic acid. The polynucleotide could be used to produce a change in a cell that can be therapeutic. The delivery of polynucleotides or genetic material for therapeutic purposes is commonly called "gene therapy".

A new method is described for forming condensed nucleic acid by having a chemical reaction take place in the presence of the nucleic acid. A process is also described of forming in the presence of the nucleic acid a polymer that has affinity to nucleic acid. Moreover, a process is described of forming an interpolyelectrolyte complex containing nucleic acids by having a chemical reaction take place in the presence of the nucleic acid. In addition, the nucleic acid-binding polymer can form as a result of template polymerization. This obviously excludes the formation of polymers such as proteins or nucleic acids or other derivatives that bind nucleic acid by Watson-Crick binding.

Previously, the occurrence of chemical reactions or the process of polymerization in the presence of the nucleic acid has been assiduously avoided when delivering nucleic acid. Perhaps, this arose out of concerns that the processes of chemical reactions or polymerization would chemically modify the nucleic acid and thereby render it not biologically active. Surprisingly, we show that we can perform polymerizations in the presence of nucleic acids without chemically modifying the nucleic acid and that the nucleic acid is still functional. For example, a plasmid construct containing a promoter and the reporter gene luciferase can still express as much luciferase as native plasmid after transfection into cells.

The process of forming a polymer in the presence of nucleic acid has several advantages. As FIG. 1 illustrates, aggregation and precipitation of the nucleic acid can be avoided by having the polymerization take place in the presence of the nucleic acid. This newly described process enabled us to form supramolecular complexes of nucleic acid and polymer rapidly, consistently, and at very high concentrations of polynucleic acid. In fact, high concentration of the template nucleic acid favors this process. In contrast, the previously described process of mixing a nucleic acid and an already-formed polycation (such as polylysine) has to be done at very dilute concentrations. In addition, the previously-described procedure requires that the mixing, salt and ionicity conditions must be carefully controlled as well. This explains why the use of polylysine-DNA complexes are not widely used for the transfer of DNA into cells and is only done in a few laboratories.

The other advantage that flows from the newly described process of having polymerization take place in the presence of nucleic acid is that polymers could form that would not be able to become associated with nucleic acids if the polymer was formed first. For example, the polymerization process could result in a hydrophobic polymer that is not soluble in aqueous solutions unless it is associated with nucleic acid. A hydrophobic moiety comprises a C6-C24 alkane, C6-C24 alkene, sterol, steroid, lipid, or hydrophobic hormone. Furthermore, the process of having the polymerization taking place in organic solvents and heterophase systems enables more types and more defined types of vesicles to be formed.

This process will enable supramolecular complexes to be more easily assembled. It will also enable novel and more defined complexes to be made. Yet another advantage that flows from this invention is that nucleic acid/polymer complexes will be smaller. The size of DNA/polymer complex is critical for gene delivery especially in vivo.

These processes can be used for transferring nucleic acids into cells or an organism such as for drug delivery. They may also be used for analytical methods or the construction of new materials. They may also be used for preparative methods such as in the purification of nucleic acids. They are also useful for many types of recombinant DNA technology. For example, they may be used to generate sequence binding molecules and protect specific sequences from nuclease digestion. Protection of specific regions of DNA is useful in many applications for recombinant DNA technology.

A preferred embodiment provides a method of making a compound for delivery to a cell, comprising: forming a polymer in the presence of a biologically active drug.

Another preferred embodiment provides a method of making a compound for delivery to a cell, comprising: cross-linking a polymer in the presence of a polyion, thereby forming a complex of polymer and polyion; and, delivering the complex to the cell.

Another preferred embodiment provides a method of making a compound for delivery to a cell, comprising: modifying a molecule in the presence of the polyion thereby providing a deliverable polyion.

Yet, another preferred embodiment provides a method of making a compound for delivery to a cell, comprising: mixing a polyion with a first polymer and a second polymer thereby forming a deliverable complex.

Further objects, features, and advantages of the invention will be apparent from the following detailed description when taken in conjunction with the accompanying drawings.

DETAILED DESCRIPTION

1. Drug Delivery

Figure 1:
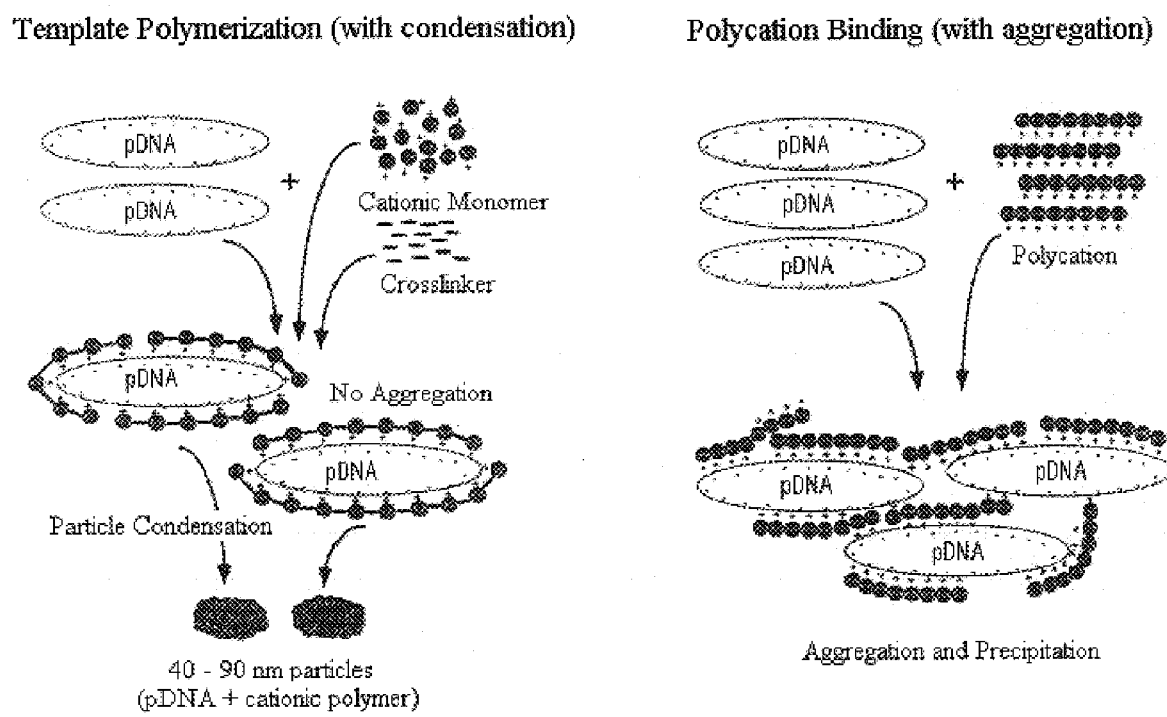
FIG. 1 is a comparison of pDNA following template polymerization and complexation contrasted with preformed polycations binding and precipitating.

A process for drug delivery is described in which polymerization and chemical reaction processes take place in the presence of the drug in order to deliver the drug. The polymer is formed from a variety of monomers in the presence of the drug and then the mixture is delivered. The mixture could undergo further purification or preparative methods. Drug delivery encompasses the delivery of a biologically active compound to a cell. This can be accomplished with prokaryotic or eukaryotic cell. It includes mammalian cells that are either outside or within an organism. It also includes the administration of the drug to the whole organism by standard routes such as intravenous, intra-arterial, intra-bile duct, intramuscular, subcutaneous, intraperitoneal, or direct injections into tissues such as the liver, brain, kidneys, heart, eyes, lymph nodes, bone, gastrointestinal tract. It also includes delivery into vessels such as blood, lymphatic, biliary, renal, or brain ventricles.

In one preferred embodiment, this process is used to deliver nucleic acids. The process of delivering nucleic acids means exposing the cell to the polynucleic in the presence of the delivery system. Cells indicate both prokaryotes and eukaryotes. The cell is located in a living organism and exposing is accomplished by administering the nucleic acid and the delivery system to the organism. It also means mixing the nucleic acids with cells in culture or administering the nucleic acids to a whole organism. Delivering nucleic acids encompasses transfecting a cell with a nucleic acid. These delivery processes include standard injection methods such as intramuscular, subcutaneous, intraperitoneal, intravenous, and intra-arterial. It also includes injections into any vessel such as the bile duct and injections into any tissue such as liver, kidney, brain, thymus, heart, eye, or skin.

Drugs, pharmaceuticals, proteins, peptides and nucleic acids are biologically active compounds. The drug can be either the template polymer or the daughter polymer. In the preferred embodiment, the template polymer is a polyion, a macromolecule carrying a string of charges, such as a nucleic acid which would be termed a polyanion because of its average negative charge. The term "nucleic acid" is a term of art that refers to a string of at least two base-sugar-phosphate combinations. Nucleotides are the monomeric units of nucleic acid polymers. The term includes deoxyribonucleic acid (DNA) and ribonucleic acid (RNA) in the form of an oligonucleotide, messenger RNA, anti-sense, plasmid DNA, parts of a plasmid DNA or genetic material derived from a virus. The term "nucleic acid" includes both oligonucleic acids and polynucleic acids. Polynucleic acids are distinguished from oligonucleic acid by containing more than 120 monomeric units. In the case of the transfer of nucleic acids into cells, the nucleic acid is the template.

The nucleic acid (polynucleotide) could also be used to produce a change in a cell that can be therapeutic. The delivery of polynucleotides or genetic material for therapeutic purposes is commonly called "gene therapy". The delivered polynucleotide could produce a therapeutic protein such as a hormone, cytokine, or growth factor. For example, the polynucleotide in the form of a plasmid DNA could produce the human growth hormone. The polynucleotide could produce an enzyme that is deficient or defective in patients with an inborn error of metabolism. For example, a plasmid DNA could produce phenylalanine hydroxylase which would be therapeutic in patients with phenylketonuria. Furthermore, the polynucleotide could supply an anti-sense that would be therapeutic in patients with a tumor, cancer, or infection. For example, the polynucleotide could be a DNA that is transcribed into an anti-sense molecule.

2. Formation of Polymers

A polymer is a molecule built up by repetitive bonding together of smaller units called monomers. In this application the term polymer includes both oligomers which have two to ~80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

Associated with the polymer in a preferred embodiment is a steric stabilizer which is a long chain hydrophilic group that prevents aggregation of final polymer by sterically hindering particle to particle electrostatic interactions. Examples include: alkyl groups, PEG chains, polysaccharides, hydrogen molecules, alkyl amines.

To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M. P. Stevens Polymer Chemistry: An Introduction New York Oxford University Press 1990).

2A. Step Polymerization

In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A–B yields -[A–B]-

Or the other approach is to have two difunctional monomers.

A–A+B—B yields -[A—A-B-B]-

Generally, these reactions can involve acylation or alkylation. Acylation is defined as the introduction of an acyl group (—COR) onto a molecule. Alkylation is defined as the introduction of an alkyl group onto a molecule.

If functional group A is an amine then B can be (but not restricted to) an isothiocyanate, isocyanate, acyl azide, N-hydroxysuccinimide, sulfonyl chloride, aldehyde (including formaldehyde and glutaraldehyde), epoxide, carbonate, imidoester, carboxylate, or alkylphosphate, arylhalides (difluoro-dinitrobenzene) or succinic anhyride. In other terms when function A is an amine then function B can be acylating or alkylating agent.

If functional group A is a sulfhydryl then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) a diazoacetate or an amine in which carbonyldiimidazole or carbodiimide is used.

If functional group A is an hydroxyl then function B can be (but not restricted to) an epoxide, oxirane, or an amine in which carbonyldiimidazole or carbodiimide or N, N'-disuccinimidyl carbonate, or N-hydroxysuccinimidyl chloroformate is used.

If functional group A is an aldehyde or ketone then function B can be (but not restricted to) an hydrazine, hydrazide derivative, aldehyde (to form a Schiff Base that may or may not be reduced by reducing agents such as $NaCNBH_3$).

Yet another approach is to have one difunctional monomer so that

A—A plus another agent yields -[A—A]-.

If function A is a sulfhydryl group then it can be converted to disulfide bonds by oxidizing agents such as iodine ($I_2$) or $NaIO_4$ (sodium periodate), or oxygen ($O_2$). Function A can also be an amine that is converted to a sulfhydryl group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, sulfhydryl, carboxylate groups yield chemical bonds that are described as amide, amidine, disulfide, ethers, esters, isothiourea, isourea, sulfonamide, carbamate, carbon-nitrogen double bond (enamine or imine) alkylamine bond (secondary amine), carbon-nitrogen single bonds in which the carbon contains a hydroxyl group, thio-ether, diol, hydrazone, diazo, or sulfone.

2B. Chain Polymerization

In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methaacrylamide groups can undergo chain reaction which can be radical, anionic, or cationic. Chain polymerization can also be accomplished by cycle or ring opening polymerization. Several different types of free radical initiatiors could be used that include peroxides, hydroxy peroxides, and azo compounds such as 2,2'-Azobis(-amidinopropane) dihydrochloride (AAP).

3. Types of Monomers

A wide variety of monomers can be used in the polymerization processes. These include positive charged organic monomers such as amines, imidine, guanidine, imine, hydroxylamine, hydrozyine, heterocycles (like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyldipropylammonium bromide (Compound 9).

1. Monomers can also be oligopeptides, polypeptides or proteins (produced synthetically or in an organism). These oligopeptides can be a NLS peptide which corresponds to the 12 amino acid nuclear localizing sequence of SV40 T antigen, fusion peptides (derived from viruses), endosomolytic peptides and amphipathic peptides. Amphipathic compounds have both hydrophilic (water-soluble) and hydrophobic (water-insoluble) parts. The amphipathic compound can be cationic or incorporated into a liposome that is positively-charged (cationic) or non-cationic which means neutral, or negatively-charged (anionic). Proteins such as histone HI can be used. Proteins that bind DNA at sequence-specific sequences such as Gal4 protein could also be used.

Monomers can also be hydrophobic, hydrophilic or amphipathic. Examples of amphipathic compounds include but are not restricted to 3,3'-diamine-N-(7-octene)-N- methyldipropylammonium bromide (Compound 7), N,N'-Dinonacrylate-N,N,N',N'-tetramethylpropanediammonium bromide (Compound 10), N,N',N''-Trinonacrylate-N,N,N',N',N''-pentamethyldiethylentriammonium bromide (Compound 11) and amphipathic peptides such as CKLLKKLLKLWKKLLKKLKC.

Monomers can also be intercalating agents such as acridine, thiazole organge, or ethidium bromide.

4. Other Components of the Monomers and Polymers

The polymers have other groups that increase their utility. These groups can be incorporated into monomers prior to polymer formation of attached to the polymer after its formation. These groups include:

a. Targeting Groups

These groups are used for targeting the polymer-drug or polymer-nucleic acid complexes to specific cells or tissues. Examples of such targeting agents include agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind cells. Lipids and steroids could be used to directly insert into cellular membranes.

b. Reporter Groups

Reporter or marker groups are molecules that can be easily detected. Typically they are fluorescent compounds such as fluorescein, rhodamine, texas red, cy 5, or dansyl compounds. They can be molecules that can be detected by UV or visible spectroscopy or by antibody interactions or by electron spin resonance. Biotin is another reporter molecule that can be detected by labeled avidin. Biotin could also be used to attach targeting groups.

c. Cleavable Groups

The polymers can contain cleavable groups within the template binding part or between the template binding part and the targeting or reporter molecules. When within the template binding part, breakage of the cleavable groups leads to reduced interaction of the template and daughter polymers. When attached to the targeting group, cleavage leads to reduce interaction between the template and the receptor for the targeting group. Cleavable groups include but are not restricted to disulfide bonds, diols, diazo bonds, ester bonds and sulfone bonds.

5. Template Polymerization

Template polymerization has been defined as the following (van de Grampel, H. T., Tan, Y. Y. and Challa, G. Macromolecules 23, 5209–5216, 1990):

"Template polymerizations can be defined as polymerizations in which polymer chains are able to grow along template macromolecules for the greater part of their lifetime. Such a mode of propagation can be achieved through the existence of cooperative interactions between the growing chain and the template chain and usually leads to the formation of an interpolymer complex. In general, a well-chosen template is able to affect the rate of polymerization as well as the molecular weight and microstructure of the formed polymer (daughter polymer). The concepts of template polymerization were described by Ballard and Bamford with the ring opening polymerization of the N-carboxyanhydride of DL-phenylalanine on a polysarcosine template. Since then, many other systems involving radical and nonradical initiation of vinyl monomers have been studied in which one or more template effects, arising from this peculiar propagation mode, were identified. A number of radical-initiated template polymerizations have been studied, employing water as solvent".

The main features of template polymerization are:

1. Complex formation takes place between polymers
2. The rate of polymerization increases as the concentration of template increases. (Fujimori, K., (1979) Makromol. Chem. 180, 1743)
3. The structure and conformational features of the template are reflected in the corresponding daughter polymer.

In template polymerization, propagation of new polymer chain occurs predominantly along the template, a macromolecular chain, through specific cooperative interaction. The nature of interaction can be electrostatic, H-bonding, charge-transfer, and Van der Waals forces in combination with steriochemical matching. The presence of template usually affects various polymerization characteristics as well as the microstructure of the polymer formed. The mechanism of template polymerization depends on the degree of monomer adsorption. Two extreme cases can be discerned: the adsorption equilibrium coefficient for monomer, $K_M$=-• (type 1) and KM=0 (type 2). In type 1 ("zip" reaction) monomer is fully adsorbed onto all template sites and the polymerization occurs only on template. As the $K_M$ constant becomes smaller, template propagation increasingly proceeds via reaction monomers from the surrounding solution at the expense of reaction with adjacently adsorbed monomer. When $K_M$=0 (type 2) only non-adsorbed monomer is present and the template macromolecules are completely solvated by solvents instead of the monomers. A prerequisite for template propagation under this condition is the growing daughter oligomer, created in bulk solution, that then complexes with template. ("pick-up" reaction). The chain length below which no complexation takes place (critical chain length) is important for magnitude of the template effect. In fact, there is no sharp border between type 1 and type 2 polymerization's.

Several processes for using template polymerization for drug delivery are described. The daughter polymer could be the drug. In a preferred embodiment, the template is the drug (defined to include pharmaceuticals, therapeutic agents or biologically active substances). The process of using template polymerization for drug delivery comprises mixing the template with monomers and having a daughter polymer forming from the monomers. The mixture of template polymer and daughter polymer is then administered to a cell by putting the mixture in contact with a cell or near a cell. The mixture of template and daughter polymer could also be placed in a pharmaceutical formulation and vial for delivery to an animal. The template polymer could be a polyanion such as nucleic acid including DNA, RNA or an antisense sequence. The DNA can produce a therapeutic agent such as a therapeutic protein or anti-sense RNA.

In a preferred embodiment, targeting groups could be added during the initial template polymerization stage or during subsequent polymerization steps. In addition, after template polymerization, networks or additional networks can be added to the polymer. These could be used to cross-link the polymers. For example, the polymer could be cross-linked to put the template into a "cage". Cross-linking is the linking of two moieties of a polymer to one another using bifunctional chemical linker. One result is that the polymer, as a network, becomes stronger and more resistant to being dissolved. Covalent linking bifunctional linkers may be homobifunctional (which involves the same chemical reaction for linking both moieties) or heterobifunctional (involves two different reactions allowing linkage of different functional groups). By cross-linking, a cage may be formed around or near the polyion creating a complex of polyion and polymer. Cross-linking the polymer protects the polyion from being destroyed by enzymes and other degrading substrates. For example: If the polyion is DNA, the cross-linked or caging polymer protects DNA from DNases.

In a preferred embodiment, stable caged polyion particles still bear a net positive charge. However, it is desirable to recharge it so it would interact less with negatively-charged polymers and particles in vivo. Recharging is switching the net polyion particle charge to an opposite charge.

Complexes may be formed and continue to function in a solution of changeable tonicity, which means that the solution can be hypotonic, hypertonic or normal tonicity. Hypotonic means any solution which has a lower osmotic pressure than another solution (that is, has a lower concentration of solutes than another solution). A hypotonic solution is the opposite of a hypertonic solution. Normal tonicity in the preferred embodiments is the tonicity of human body fluids, specifically blood.

6. Homophase and Heterophase Polymerization

The chemical reaction and polymerization processes can take place in homophase systems in which the monomer and nucleic acid are in the same solution. This solution can be water, alcohol, chloroform, esters, organic solvents, or polar aprotic solvents such as DMF or DMSO or dioxane. They can be mixtures of aqueous and organic solvents.

The chemical reaction and polymerization processes can take place in heterophase systems in which the nucleic acid is in one phase and the monomer is in another phase. Such heterophase systems can be "oil in water" and also "water in oil" where oil is defined as a solvent that has low solubility in water. This approach could enable the formation of micellar-like structures that have the hydrophobic parts of the polynucleotide in the inside of a vesicle and the hydrophilic parts on the outside, or vice-versa. The polymerization reaction can be performed in both direct (oil-in-water) and inverse (water-in-oil) emulsions. This approach allows the use of hydrophobic or amphipathic monomers (Blackley, D.C. Emulsion Polymerization, London: Appl. Sci., 1975). Heterophase polymerization enables vesicles, particles, or supramolecular complexes to be produced in which the nucleic acid is on the surface of polymer micelles or the nucleic acid is inside of monolayer inverse polymer micelles. In the last case different lipids can be used for external layer formation. Inverse phase emulsion can be prepared so that in average only one molecules of biopolymer will be present in every water drop.(Martinek, K., Levashov, A. V., Klyachko, N., Khmelnitski, Y. L., & Berezin, I. V. (1986) Eur. J. Biochem. 155, 453–468).

7. Supramolecular Complexes

A supramolecular complex is a structure that contains two or more different molecules that are not covalently bound. Supramolecular complexes can be used for drug delivery and for other purposes such as for preparative or analytical methods or the construction of new materials. We describe a new method for forming a supramolecular complex containing nucleic acid and a polymer in which the polymer is formed in the presence of the nucleic acid.

The supramolecular complex can contain other components in addition to the nucleic acid and polymer. It can contain another polymer that is already formed. This already formed polymer can bind the nucleic acid or the daughter polymer. The additional component can be a protein. This protein can be cationic and contain positive charges that enables it to bind nucleic acid. Such cationic proteins could be histone, polylysine, or protamine. The supramolecular complex could also contain targeting groups.

A supramolecular complex formed in this fashion could contain amphipathic compounds that could be part of liposomes, micelles, or inverse micelles. Liposomes are microscopic vesicles that contain amphipathic molecules that contain both hydrophobic and hydrophilic domains. Liposomes can contain an aqueous volume that is entirely enclosed by a membrane composed of lipid molecules (usually phospholipids) (R. C. New, p. 1, chapter 1, "Introduction" in Liposomes: A Practical Approach, ed. R. C. New IRL Press at Oxford University Press, Oxford 1990). Micelles and inverse micelles are microscopic vesicles that contain amphipathic molecules but do not contain an aqueous volume that is entirely enclosed by a membrane. In micelles the hydrophilic part of the amphipathic compound is on the outside (on the surface of the vesicle) whereas in inverse micelles the hydrophobic part of the amphipathic compound is on the outside.

8. Condensed Nucleic Acids

A method of condensing nucleic acid is defined as decreasing the linear length of the nucleic acid. Condensing nucleic acid also means compacting nucleic acid. Condensing nucleic acid also means decreasing the volume which the nucleic acid molecule occupies. A example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures are rendered partially resistant to nuclease (DNase) action. The condensed structures can also be seen on electron microscopy.

The process of condensing nucleic acid can be used for transferring nucleic acids into cells or an organism such as for drug delivery. It could also be used for prepartive or analytical methods or the construction of new materials.

We describe a new method for forming condensed nucleic acid by having a chemical reaction take place in the presence of the nucleic acid. A chemical reaction is defined as a molecular change in the participant atoms or molecules involved in the reaction. An example of a molecular change would be the breaking and forming of covalent bonds of participant compounds. Covalent bonds are defined as having shared-electron bonds such as those found in carbon-carbon, carbon-nitrogen, carbon hydrogen, carbon-oxygen, carbon-sulfur, carbon-halogen, nitrogen-hydrogen, oxygen-hydrogen, oxygen-oxygen and sulfur-oxygen bonds. The chemical reaction(s) could result in a polymer being formed.

The polymerization process could take place by the process of template polymerization. A supramolecular complex could form as a result of this process.

In a preferred embodiment, one method utilizes covalently attaching compounds to polyions such as genes for enhancing the cellular transport of the polyion while maintaining its functionality. A patent application entitled: A Method For Covalent Attachment Of Compounds To Genes, Serial No. 08/990,015, filed Dec. 12, 1997 now U.S. Pat. No. 6,093,701 describing methods of covalently attaching compounds as well as structures used therein is incorporate herein by reference. Although the cited application teaches the attachment of compounds to genes, the methods and structures may be applied to attaching molecules to a polymer as discussed in the present specification and the term polymer is not limited to nucleic acids.

Signals that enhance release from intracellular compartments (releasing signals) can cause polyion release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin At and the ER-retainingsignal (KDEL sequence), viral components such as influenza virus hemagglutinin subunit HA-2 peptides and other types of amphipathic peptides.

Nuclear localizing signals enhance the entry of a polyion into the nucleus or directs the gene into the proximity of the nucleus. Such nuclear transport signals can be a protein or a peptide such as the SV40 large T ag NLS or the nucleoplasmin NLS.

9. A Method for Forming a Polymer that Binds Nucleic Acids

We describe a process of forming in the presence of the nucleic acid a polymer that has affinity to nucleic acid. This excludes the process of forming polymers that are proteins or nucleic acids. It also excludes polymers that bind the nucleic acid by Watson-Crick binding. Watson-Crick binding is defined as the normal base-pairing arrangement in which guanine base pairs with cytosine base and in which the adenosine base pairs with thymine bases. Affinity indicates that the polymer is attracted to nucleic acid and remains bound to it by non-covalent forces (such as van der waal, hydrogen bonds, and ionic bonds) under either physiologic or non-physiologic conditions.

The process of forming a polymer in the presence of the nucleic acid can be used for transferring nucleic acids into cells or an organism such as for drug delivery. It could also be used for preparative or analytical methods or the construction of new materials.

The nucleic acid-binding polymer can form as a result of template polymerization.

We also describe a process of forming an interpolyelectrolyte complex containing nucleic acids by having a chemical reaction take place in the presence of the nucleic acid. An interpolyelectrolyte complex is defined as a mixture of two polymers with opposite charges. In this situation the nucleic acid is a polyanion and the formed polymer is a polycation. Definitions of Compounds Used in Preferred Embodiments Orthogonal—Refers to a protective (protecting) group that can be selectively removed in the presence of other protective groups contained on the molecule of interest.
Monovalent—refers to an ionic species possessing 1 charge.
Protective Group—A chemical group that is temporarily bound to functionalities within a multifunctional compound that allows selective reactions to take place at other sites within the compound. Common protective groups include, but are not limited to carbamates, amides, and N-alkyl groups.
Functionality—Refers to general classes of organic compounds such as: alcohols, amines, carbonyls, carboxyls, and thiols.

EXAMPLES

Overview of Experimental Design

The following examples show that polymerization can take place in the presence of DNA. Since the central feature of these polymers is their ability to bind DNA, we selected a relatively simple assay to detect the formation of such polymers and that is agarose gel electrophoresis with ethidium bromide staining of DNA. A strong DNA-binding polymer retards (or slows) the migration of the DNA in the gel. In the experimental samples where the DNA is already present during the polymerization (reaction) process, the sample is simply loaded onto the agarose gel. In the control samples where DNA is not present during the reaction process, the DNA is added after the reaction. This approach is also a powerful method to determine whether any polymer is formed by a template polymerization process. That is, if the polymer only forms when the template DNA is present and not when the template DNA is absent then this is definitive proof of template polymerization. The initial results with agarose gel electrophoresis are followed up with more sophisticated assay for polymers and particles that include gel filtration (size exclusion) chromatography, transmission electron microscopy, and particle sizing by dynamic light scattering.

The process of polymerization in the presence of nucleic acids can be used to transfer and express genes in cells. Besides showing the utility of this process, it also indicates that the chemical reactions were not chemically modifying or destroying the nucleic acid. A another approach was also used to detect nucleic acid damage. We incorporated disulfide bonds into the polymers and then broke the polymers down by adding dithiothreitol (DTT also known as Cleland's reagent) which reduces the disulfide bonds. After the breakdown of the polymers the nucleic acid, DNA (that was within the polymer particles) was transfected into cells using another transfection method (with a cationic lipid). Expression was the same as the native DNA. Expression is a very sensitive indicator of any destruction or modification along the entire length of the reporter (luciferase) gene and promoter. These polymers were designed with disulfide bonds so that they could more easily be broken down inside cells.

EXAMPLE 1

Step polymerization with DNA as a template was performed using the polyamine N,N'-bis(2-aminoethyl)-1,3-propanediamine (AEPD) and dithiobis (succinimidylpropionate) (DSP). This template polymerization was done using two different monomer species together in which each of the species possessed at least two reactive ends to propagate a growing chain. Using a bifunctional amine with affinity to plasmid DNA as a monomer and bifunctional aminoreactive cross-linker as a co-monomer, we demonstrated that 1) it is possible to obtain DNA-bound polyamide as a result of such polymerization, and 2) the resulting polymer can condense template DNA into compact structures.

Methods:

The following amine was used as monomers:
1. N,N'-bis(2-aminoethyl)-1,3-propanediamine (AEPD, Aldrich, Milwaukee, Wis.)

The following cross-linker was used as a co-monomer:
1. Dithiobis(succinimidylpropionate), (DSP, S-S cleavable bis succinimide ester, Pierce, Rockford, Ill.)

Optimized reaction conditions with AEPD/DSP were as follows. Plasmid DNA (pCIluc, 50 mg) and AEPD (10 mg) were mixed in 50 ml of buffer solution (0.1 M HEPES, 1 mM EDTA, pH 7.4). After 5 min DSP (60 mg in 1.5 ml of dimethylformamide) was added. After mixing, the reaction was left for 1 hour in the dark at room temperature. Finally, reaction mixture was dialysed against water or desired buffer solution in microdialysis cell with a molecular weight cut-off of 1,000 (Rainin, Ridgefield, N.J.).

The pCILuc plasmid expresses a cytoplasmic luciferase from the human immediately early cytomegaloviral (CMV) promoter. It was constructed by inserting the cytoplasmic luciferase cDNA into the pCI (Promega Corp., Madison, Wis.) CMV expression vector. Specifically, a Nihau/EcoRI restriction digestion fragment containing the cytoplasmic luciferase cDNA was obtained from pSPLuc (Promega Corp.) and inserted into pCI pDNA that was digested with NheI and EcoRI. Plasmid DNA was purified using the Qiagen (Chatsworth, Calif.) plasmid purification system (alkaline lysis followed by anion exchange chromatography).

Agarose gel electrophoresis and ethidium bromide staining of the DNA was done using standard techniques (Sambrook, J., Fritsch, E. F., and Maniatis, T. (1989) in Molecular Cloning Cold Spring Harbor Laboratory Press, Cold Spring Harbor, N.Y.).

Standard gel filtration (size-exclusion) chromatography was performed to determine the size of the polymers that formed in the presence and absence of DNA. Since the DNA strongly bound the polymer, it was necessary to first remove the DNA. This was accomplished by vigorous DNase digestion. Samples of DNA/AEPD/DSP reaction mixture (50 ug total DNA, pCIluc) were supplemented with 5M NaCl solution up to 0.5 M NaCl. DNase I (Sigma) was added to the mixture (0.06 U/ug DNA). DNase digestion was carried out in the buffer containing 10 mM Tris, 10 mM MgCl2, 1 mM CaCl2, pH 7.0, for 4 hrs at 37° C. After this reaction, the mixture was centrifuged at 12,000 rpm for min and applied on the Sephadex G-75 (Sigma) column (0.8×20 cm) equilibrated with mM HEPES, 0.5 NaCl, pH 7.4. Fractions (0.5 ml) were analyzed for OD 260.

Transmission electron microscopy of the formed complexes using standard negative staining procedures on coated grids. After the samples were stained with methylamine tungstate (BioRAD), the grids were examined using a Jeol 100CX transmission electron microscope.

The preparation for light scattering was prepared essentially with the same DNA/AEPD/DSP ratios as for EM (see optimized AEPD/DSP) but with 3 mg of DNA (pCIluc). DNA/AEPD mixture was incubated with occasional vortexing for 10 min at room temperature before addition of DSP. The sample was centrifuged at 12,000 rpm for min and passed through 0.2 um polycarbonate filter (Poretics Corp., Livermore, Calif.) and analyzed using Particle Size Analyser equipped with 15 M argon laser (Brookhaven Instruments, Inc.).

Results:

Agarose gel electrophoresis of the final experimental complexes (formed by reacting AEPD and DSP in the presence of DNA) demonstrated characteristic gel retardation of plasmid DNA in the gel in which the complexed plasmid DNA migrated more slowly than the original plasmid DNA. In addition there was some DNA material in the starting well. The final complexes were also treated with 25 mM dithiothreithol (DTT) (Fisher, Itasca Ill.) for 30 minutes at 37° C. to cleave the disulfide bonds within the polymer (part of the DSP co-monomer). The DTT treatment reversed the electrophoretic pattern back to that of the native plasmid DNA and no retarded DNA material was present. This indicates that the retarded pattern was due to the polymer complexing with the DNA. It also indicates that the monomers or polymer did not react with the DNA. Transfection of the DNA (after DTT treatment) into cells in culture using a commercial transfection reagent (LT-1, Mirus, Madison, Wis.) resulted in as much luciferase expression as native DNA. This also indicates that the DNA was not chemically modified.

A control sample contained AEPD and DSP at the same concentrations but plasmid DNA was omitted during the reaction. The DNA was added after the reaction was completed. Agarose gel electrophoresis showed much less retardation of the DNA than the above experimental sample. This indicates that polymerization did not occur in the control sample and that the polymerization observed in the experimental sample occurred by template polymerization.

Further studies were performed to determine the size of the polymer that formed in the presence of the DNA. This was accomplished by first digesting the DNA exhaustively with DNase and then running the remaining polymer through a size-exclusion column. Gel filtration of the complex's exhaustive DNase lysate in 0.5 M NaCl demonstrated formation of the product with apparent molecular weight of >3,000 Da. The control sample (DNA added after reaction of AEPD and DSP) did not contain any large polymer of this molecular weight. This indicates that the polymer that formed in the presence of DNA occurred by template polymerization.

Figure 2:
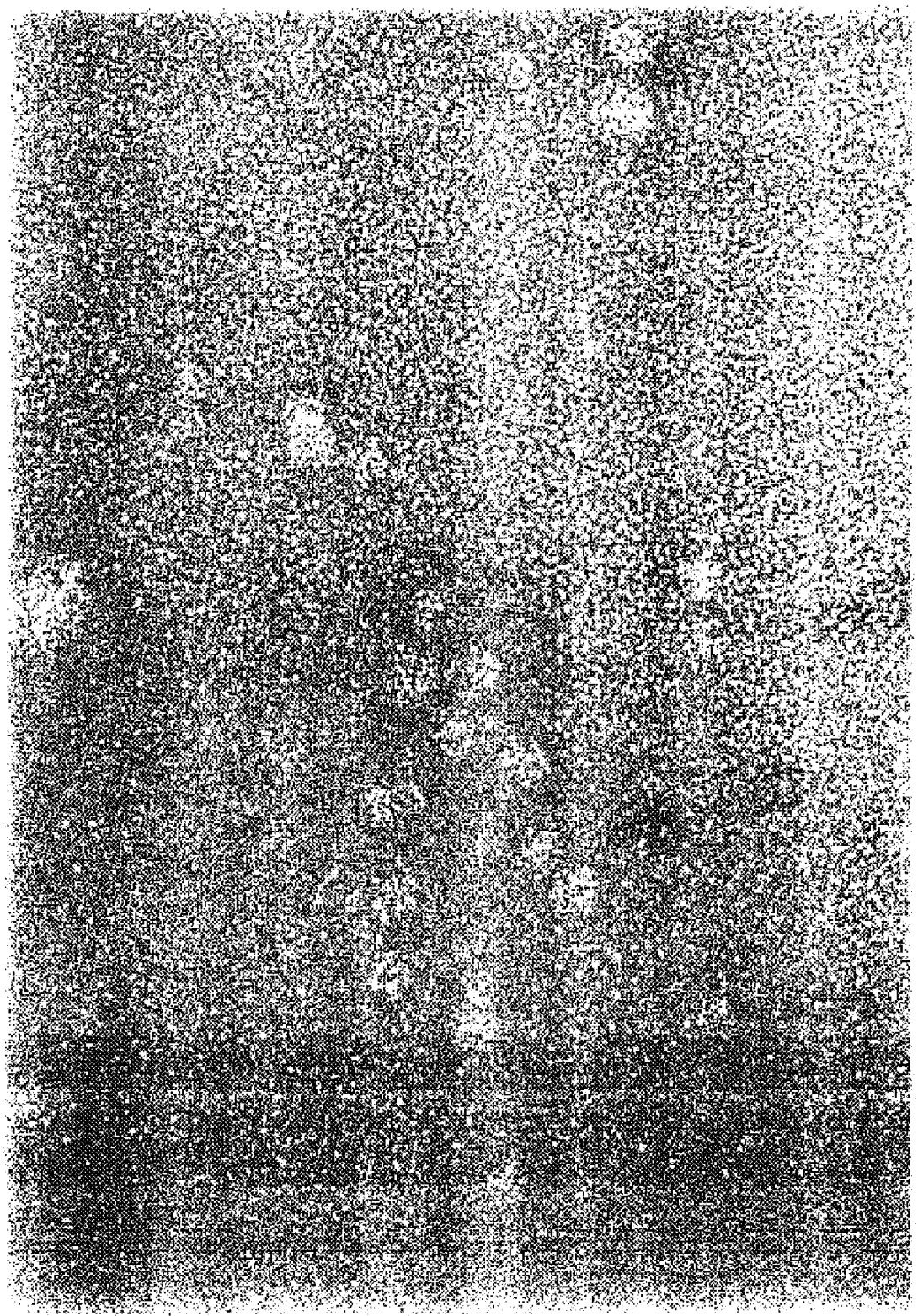
FIG. 2 shows complexes ranging in size from 40–70 nanometers in diameter after being dried onto carbon grids and stained with methylamine tungstate.

Physical methods were employed to determine directly the size and shape of the polymer/DNA complexes. Transmission electron microscopy of the experimental complexes (formed by reacting AEPD and DSP in the presence of DNA) revealed formation of spherical structures with 40–50 nm in diameter (individual and aggregated) (FIG. 2). Dynamic light scattering of the same preparation yielded average particle size of 80 nm. These results are consistent with the ability for the particles to pass through 0.2 micron filters. The control samples (DNA added after reaction of AEPD and DSP) did not contain any particles on electron microscopy or particle sizing.

Findings:
1. The polyamine was co-polymerized with DSP to form a polymer in the presence of DNA and this polymer was bound to the DNA.
2. The polymer formed by a process of template polymerization.
3. The polymer condensed the DNA to form particles less than 80 nm in diameter.
4. The DNA was not chemically modified by the polymerization process and was still able to express luciferase after transfection into cells in culture.

EXAMPLE 2

Step polymerization with DNA as a template was performed using the polyamine N,N'-bis(2-aminoethyl)-1,3-propanediamine (AEPD) as in Example 1 above except DPBP was used as the co-monomer.

Methods:

The following amine was used as monomers:
1. N,N'-bis(2-aminoethyl)-1,3-propanediamine (AEPD, Aldrich, Milwaukee, Wis.)

The following cross-linker was used as a co-monomer:
1. Dimethyl-3,3'-dithiopbispropionimidate (DPBP, S-S cleavable bisimido ester, Pierce)

Optimized reaction conditions with AEPD/DPBP were as follows. Plasmid DNA (pCIluc, 50 mg) and AEPD (24 mg) were mixed in 150 ml of buffer solution (20 mM HEPES, 1 mM EDTA, pH 7.4). After 5 min DPBP (155 mg in 5 ml of methanol) was added. After mixing, the reaction was left for 1 hour in the dark at room temperature.

Results:

Unlike the bissuccinimidate reaction (example 1), diimidoester cross-linking (used in this example) preserves positive charges of aminogroups by converting them into amidines. Therefore, extremely positively charged polymer was formed as a result of this reaction which caused complete DNA retardation on agarose gels. DNA addition to the reaction mixture after the reaction between amine and cross-linker did not induce DNA retardation on the gel. Treatment of retarded complexes with DTT resulted in restoration of the native plasmid electrophoretic pattern.

Findings:
1. Step polymerization of AEPD and DPBP occurred in the presence of DNA and resulted in a polymer that bound DNA very strongly.
2. The polymer formed by template polymerization.
3. The DNA was not chemically modified and could be recovered intact after DTT treatment.

EXAMPLE 3

Step polymerization with DNA as a template was performed using the polyamine N,N'-bis(2-aminoethyl)-1,3-propanediamine (AEPD) as in Example 1 above except 2-iminothiolane (Traut's reagent) was used as the co-monomer. This is an example of ring opening of the 2-iminothilane and then oxidation of SH groups that form as a result of the ring opening.

Methods:

The following amine was used as monomers:
1. N,N'-bis(2-aminoethyl)-1,3-propanediamine (AEPD, Aldrich, Milwaukee, Wis.)

The following cross-linker was used as a co-monomer:
1,2-iminothiolane (thiol/amino-linking heterobifunctional agent, Pierce)

Optimized reaction conditions with AEPD/2-iminothiolane were as follows. Plasmid DNA (pCILuc, 50 mg), AEPD (1 mM) and iminothiolane (4 mM) were mixed in 450 ml of buffer solution (20 mM HEPES, 1 mM EDTA, pH 8.0). After 30 min 5 ml of iodine solution (40 mM in ethanol) were added. Reaction was allowed to stand for 1.5 h in the dark at room temperature.

Results:

Generally, the above procedure is two-step polymerization with reactive monomer formation. 2-iminothiolane forms bisthiol AEPD derivative on the DNA which can be further polymerized by oxidizing SH groups with molecular iodine. Results for DNA gel retardation and DTT treatment are basically the same as for AEPD/DPBP pair. Under conditions indicated above DNA and AEPD/2-iminothiolane polymer form truly soluble complex completely retarded in agarose gel.

The DNA in the control sample (DNA added after the polymer reaction) was not retarded on gel electrophoresis.

Findings:
1. Ring opening and two-step polymerization processes can be used for forming template polymers that bind to DNA.
2. Polyamines can be polymerized in the presence of DNA using the conversion amines to SH groups with subsequent oxidation reactions.

EXAMPLE 4

Similar results were obtained when spermine was used instead of AEPD as in Example 1. Plasmid DNA (10 ug) and spermine (1.5 ug) were mixed in 15 ul of 0.1M HEPES, pH 8.0. After 5 min of incubation DSP (25 ug in 1 ml of DMF) was added with intensive mixing. After 1 hr incubation at room temperature DNA was analyzed on agarose gel. In case of "DNA after" experiment, DNA (10 ug) was added after quenching DSP reaction with 0.1 M glycine for 0.5 hr. Electrophoretic pattern was found similar to the one with AEPD/DSP in Example 1.

EXAMPLE 5

A novel amine was used as a monomer in conjunction with DTBP for template polymerization of DNA.

Methods:

The following amine was used as a monomer:
1,3,3'-(N',N"-tert-butoxycarbonyl)-N-(7-octene)-N-methyldipropyl-ammonium bromide (compound 7, see synthesis section).

Following cross-linkers were used as co-monomers:
1. Dimethyl-3,3'-dithiopbispropionimidate (DTBP, S-S cleavable bisimido ester, Pierce)

Optimized reaction conditions with compound 6/DTBP were as follows. Plasmid DNA (pCILacZ, 10 mL of a 3.4 mg/mL stock solution, 34 mg, 103 nmol nucleotide base) and compound 6 (3 mL of a 1.29 mg/mL stock solution, 39 mg, 108 nmol) were mixed with 85 ml water and 10 ml of buffer solution (0.2 M HEPES, 10 mM EDTA, pH 8.0). DTBP (1.1 mL of a 100 mM solution in DMF, 33.7 mg, 109 nmol) was added. After mixing, the reaction was left for 1 h in the dark at room temperature.

The pCILacZ plasmid was similarly constructed by placing the restriction digestion fragment of the *E. coli* β-galactosidase gene into the pCI vector.

Results

Agarose gel electrophoresis of the final complexes demonstrated characteristic retardation of the plasmid DNA. The control sample (DNA added after reaction) did not show any retardation.

EXAMPLE 6

A peptide was used as a monomer for polymerization in the presence of DNA and this process enable the formation of complexes that expressed luciferase after transfection into cells in culture.

Methods:

NLS peptide corresponds to the 12 amino acid nuclear localizing sequence of SV40 T antigen. This peptide was synthesized by Genosys Biotechnologies Inc with a Cysteine on each end for cross-linking purposes (MW=1481) Histone Hi was obtained from Sigma. The cross-linkers DSP (dithiobis[succinimidylpropionate]) and DPDPB (1,4-Di-[3'-(2'-pyridyldthio)-propionamido)]butane) were purchased from Pierce.

The NLS peptide was mixed with plasmid DNA (pCILuc) at various ratios (0.4, 0.8, 1.2, 1.6) in 20 mM HEPES pH 7.5, 1 mM EDTA at a concentration of plasmid DNA of 0.3 mg/ml. The disulfide cleavable cross-linker DPDPB was added to final concentrations of 2 and 6 mM and the mixtures were incubated for 30 minutes at room temperature in the dark. Reaction products were analyzed by agarose gel electrophoresis and DNA was visualized by ethidium bromide staining. Extent of polymerization of cationic monomers (NLS peptides) was determined on SDS-PAGE. Briefly, NLS peptide/pDNA complexes (with and without DPDPB cross-linker) were incubated with 2.5 units DNase I for 1 hour at 37° C. to remove the DNA from the complexes. Following digestion, remaining protein components were run on a 15% SDS-PAGE and stained with coomassie blue.

All transfections were performed in 35 mm wells using 2 ug pDNA per well. NLS peptide/pDNA complexes (with and without DPDPB cross-linker) were diluted in Opti-MEM (Life Technologies) and a fusogenic cationic polyamine (ODAP, Mirus Corp, Madison, Wis.) was added to enhance transfection. It is believed that this polyamine helps facilitate intracellular endosomal escape of the complexes into the cytoplasm. Pre-formed complexes were incubated with phosphate buffered saline washed NIH3T3 cells for 4 hours at 37° C. Transfection complexes were then removed and replaced with complete growth medium. Cells were grown for 40–48 hours and harvested and assayed for reporter gene expression (luciferase).

For determination of luciferase activity, cells were lysed by the addition of 100 ul for 25 mm-in-diameter plates and 200 ul for 35 mm-in-diameter plates of lysis buffer (0.1% Triton X-100, 0.1M K-phosphate, 1 mM DTT pH 7.8). 20 ul of the cellular extract were analyzed for luciferase activity as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used. Results:

The stepwise cross-linking of NLS peptides along the DNA template drastically alters the mobility of pDNA in agarose gel electrophoresis. At low peptide to pDNA ratios (0.4:1, 0.8:1) the NLS peptide/pDNA/DPDPB complexes migrated as a characteristic smear with several prominent bands as compared to NLS peptide/pDNA complexes without cross-linker which migrated similarly to pDNA alone. At higher ratios (1.2:1, 1.6:1) the net charge of the complexes becomes positive and precipitation occurs with or without the DPDPB cross-linker. When the pDNA is added after the polymerization reaction (NLS peptide/DPDPB) the agarose gel migration pattern looks nearly identical to NLS peptide/ pDNA complexes without cross-linker indicating that polymerization did not occur without the template.

Figure 3:
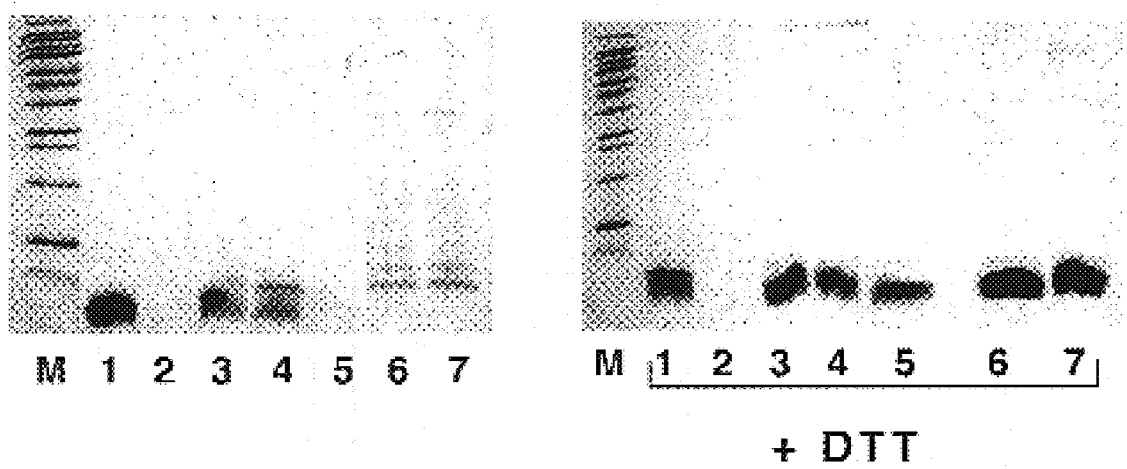
FIG. 3 illustrates template dependent polymerization of NLS Peptides using SDS-PAGE.

To determine the degree of polymerization of the NLS peptides within the NLS peptide/pDNA/DPDPB complexes, products were analyzed on 15% SDS-PAGE (without reducing agents) after DNA removal (by DNase I digestion) as illustrated in FIG. 3. Multimers of the NLS peptide were observed only in the reactions when cross-linker and template (PDNA) were present together with the NLS peptide monomers (panel A, lanes 6 and 7). With DTT (50 mM) treatment prior to SDS-PAGE the NLS peptides in the template polymerized reactions migrated at positions corresponding to monomers once again (panel B, lanes 6 and 7) indicating that disulfide bonds were present in the linkages between the monomers. Lanes: M-marker protein standards; 1—NLS peptide alone (7 μg); 2—DNase I alone (2.5 u); 3—NLS peptide/pDNA; 4—NLS peptide/DPDPB (2 mM)+ pDNA added after the polymerization reaction; 5—NLS peptide/DPDPB (6 mM)+pDNA added after the polymerization reaction; 6—NLS peptide/DPDPB (2 mM)/pDNA; 7—NLS peptide/DPDPB (2 mM)/pDNA. Protein staining clearly shows a ladder of increasing size bands indicating a stepwise polymerization of NLS peptides with dimers appearing as the fastest migrating species. This ladder of bands was only observed in the reactions when the cross-linker (DPDPB) was present together with the pDNA and the NLS peptide indicating that polymerization proceeded in a template dependent fashion. In addition, treatment of the complexes with the reducing agent DTT in the sample buffer completely abolished the ladder indicating that the ladder was a result of NLS peptide cross-linking via the disulfide containing DPDPB.

Polyamine mediated transfections performed with NLS peptide/pDNA/DPDPB complexes resulted in increased level of luciferase production as compared to transfections with NLS peptide/pDNA alone or NLS peptide/DPDPB polymerization prior to pDNA addition (Table 1). For example, with the 0.8:1 ratio of peptide to DNA compare the luciferase levels in the control sample (9.4 million, second row, NLS+2 mM DPDPB, DNA added after reaction) to the levels in the experimental sample (365.9 million, third row, NLS +2 mM DPDPB in the presence of DNA). The process of template polymerization caused a ~40-fold increase in expression.

TABLE 1

Luciferase expression (in light units per 35 mm well).

| | Total Light Units per 35 mm well × 10⁶ | |
| --- | --- | --- |
| Condition | 0.4:1 ratio of peptide to DNA | 0.8:1 ratio of peptide to DNA |
| NLS + 2 mM DPDPB, DNA added after reaction | 4.4 | 9.4 |
| NLS + 2 mM DPDPB in the presence of DNA | 10.9 | 365.9 |
| NLS + 6 mM DPDPB in the presence of DNA | 5.7 | 393.1 |

Findings:
1. Peptides can be used for template polymerization in the presence of DNA.
2. This process enables complexes to be prepared that can transfect mammalian cells efficiently.

EXAMPLE 7

Chain Polymerization using 1-Vinylimidazole (VIm) as a Monomer, 2,2'-Azobis(-amidinopropane)dihydrochloride (AAP) as an Initiator and Plasmid DNA as a Template Methods:

The conditions for template polymerization of 1-vinyl imidazole (VIm) as a monomer using 2,2'-Azobis(-amidinopropane) dihydrochloride (AAP) as an initiator were as follows. A 400 mM stock solution of VIm (TCI America OGBO1, MW 94.72, density 1.04) was prepared with sterile deionized water. The pH was adjusted to 6 with HCl. Then the solution was degassed with nitrogen gas. A 200 mM stock solution of AAP (Wako 11 G2606, MW 271.2) was also prepared with sterile deionized water and degassed with nitrogen gas. 20 mM of plasmid DNA (pBlueRSVLux, 800 ul of 6.9 mg/ml) was mixed with 20 mM of VIm and 2 mM of AAP from the stock solutions above. A control sample contained VIm and AAP at the same concentrations but plasmid DNA was omitted. Both the experimental (VIm/AAP/DNA) and control (VIm/AAP but no DNA) reactions were performed in sterile deionized water. The reactions were incubated for 2 hours at 50° C. and then the samples were analyzed by agarose gel electrophoresis followed by ethidium bromide staining. 20 mM of plasmid DNA was added to the control sample prior to loading it on the gel.

The previously described, plasmid DNA pBlueRSVLux (also known as pBS.RSVLux) was used to express the firefly luciferase reporter gene from the Rous Sarcoma Virus (RSV) LTR promoter (Danko, I., Fritz, J. D., Jiao, S., Hogan, K., Latendresse, J. L., and Wolff, J. A. Gene Therapy Pharmacological enhancement of in vivo foreign gene expression in muscle. volume 1, pp. 114–121, 1994). The plasmid also contains the SV40 intron and poly A addition signals for proper and efficient mRNA processing.

Results:

The agarose gel electrophoresis analysis showed that the plasmid DNA in the control sample (DNA added after the reaction) migrated with the same pattern as the original plasmid DNA. In the experimental sample (DNA present during the reaction), the plasmid DNA was retarded with DNA bands migrating slower than the original-plasmid DNA. There was also DNA staining material in the starting wells.

Findings:
1. A polyvinyl imidazole polymer formed in the presence of DNA and this polymer was complexed with the DNA as evident by gel electrophoresis analysis.
2. This polymer formed by template polymerization because the polymer did not form if the template DNA was omitted.

EXAMPLE 8
Template Polymerization (Caging) of Large Polymers

Methods:
Poly-L-lysine (hydrobromide, molecular mass from 30 to 70 kDa) (PLL) and Polyallylamine (hydrochloride) (55 kDa) (PAA) were obtained from Aldrich. Histone Hl(Type III-S from Calf Thymus) was obtained from Sigma. Dimethyl 3,3'-dithiobispropionimidate(DTBP) was purchased from Pierce. The polycations were dissolved in de ionized water: PLL and H1 to concentration 10 mg/ml and PAA to 2 mg/ml. DTBP was dissolved in $H_2O$ (30 mg/ml) immediately before utilization.

DNA/polycation complexes were prepared by the rapid mixing of 37 $\mu$g of plasmid DNA with varying amounts of polycations in 750 $\mu$l of 25 mM HEPES pH 8.0, 0.5 mM EDTA. The mixtures were kept 30 min at room temperature and various amounts of DTBP were added. The mixtures were incubated 2 hours at room temperature. 2M NaCl was added to the complexes to final concentration 100 mM while vigorously mixing.

Ninety degree light scattering measurements were performed using a Fluorescence Spectrophotometer. The wavelength setting was 600 nm for both the incident beam and detection of scattering light. The slits for both beams were fixed at 2 nm. The size of the resulting complex was determined by light scattering on a Brookhaven ZetaPlus particle sizer. The samples were centrifuged at 12,000 g for 7 min. The amount of DNA remaining in the supernatant was determined by measurement of the absorbency at 260 and 280 nm.

Results:
Effect of DNA/PLL Ratio and NaCl on the Light Scattering.

Figure 4:
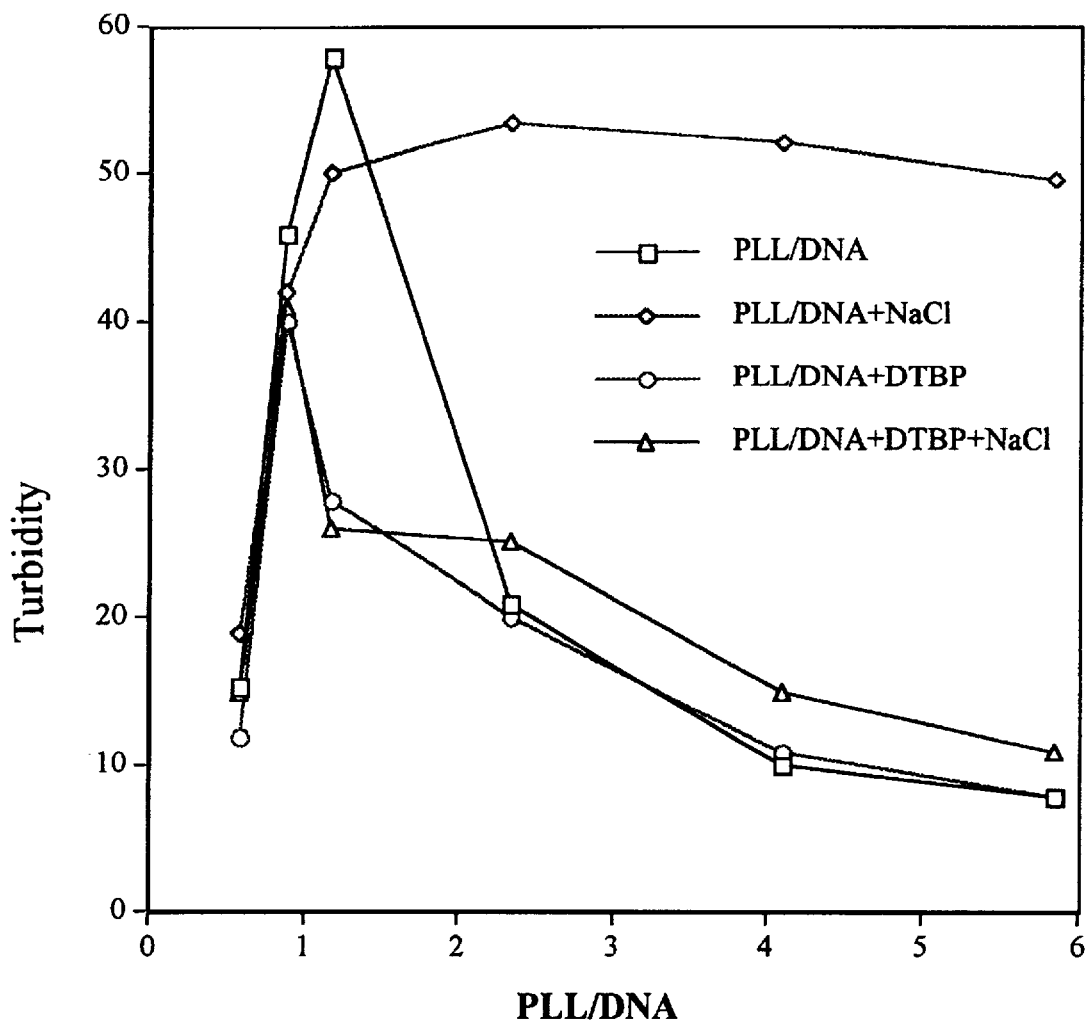
FIG. 4 illustrates the relationship between turbidity (an indication of aggregation) and the molar charge ratio of polylysine (PLL):plasmid DNA without and with 100 mM NaCl and without and without template polymerization/caging (indicated by +DTBP).

PLL was added to plasmid DNA in 0.75 ml of 25 mM HEPES pH 8.0 while vigorously mixing. The kinetics of light scattering was determined immediately after mixing. The turbidity of DNA/PLL complexes was well above that of free DNA in all range of PLL concentration As shown in FIG. 4 complex aggregation increased when molar charge ratio PLL/DNA to approximate to 1 and was maximal at ratio 1.17. Further increases in PLL concentration resulted in decreasing of complex turbidity. The light scattering did not change with time for at least for 30 min.

At low positive to negative charge ratio water-soluble nonstochiometrical complexes are formed. At ratio 1 the complexes become insoluble. Increasing the content of polycation may lead to the complex changing its sign and becoming soluble again. Presumably the particles are stabilized in solution by the positively charged loops and dangling tails of the polycation bind to the chain DNA. With increasing salt concentration to 100 mM the charge stabilized complexes (ratio +/− more then 1) started to aggregate (FIG. 4). The velocity of aggregation decreased with increasing PLL/DNA ratio, but final turbidity level was the same for all samples.

Effect of DTBP on DNA/PLL Complexes Light Scattering.

The incubation of DNA/PLL complexes with 0.97 umol of DTBP for 2 h at room temperature resulted in a shift of turbidity maximum to a PLL/DNA ratio of 0.88 (FIG. 4). That can be explained as increasing of PLL charge as a result of modification. Apparently, DTBP did not crosslink PLL/DNA complexes with each other at ratio more then 1. The addition of NaCl to a concentration of 100 mM did not change light scattering throughout the range of PLL concentration (FIG. 4). These results indicate that the addition of DTBP prevented the PLL/DNA complexes from aggregating in 100 mM salt.

The ability to centrifuge the DNA was used as another indication of aggregation (Table 2). All samples were centrifuged 7 min at 12,000 rpm and the amount of DNA in supernatant was determined. As shown crosslinked PLL/DNA complexes with molar ratio 4.1 and 5.9 did not precipitate. Therefore the size of complexes were very small. In contrast, DNA in noncrosslinked complexes were completely precipitated.

TABLE 2

The effect of DTBP on the precipitation of plasmid DNA/PPL complexes in the presence of 100 mM NaCl.

| | % DNA in solution after centrifugation | |
|---|---|---|
| PLL/DNA ratio | −DTBP | +DTBP |
| 0.585 | 67 | 77 |
| 0.879 | 0 | 0 |
| 1.171 | 0 | 0 |
| 2.342 | 0 | 17 |
| 4.098 | 0 | 97 |
| 5.854 | 0 | 97 |

Effect of PLL/DNA Ratio on the Size of Complexes.

TABLE 3

The effect of varying the DNA/PLL charge (monomoer:monomer) ratio on the sizes of PLL/DNA complexes with the addition of 0.97 umol DTBP. The sizes were determined by quasi elastic light scattering and numbers indicate the percent of particles <100 nm or >100 nm. Number in parentheses indicate the size (diameter in nm) of the most abundant species within that size range.

| | Percentage of Particles Less or Greater Than 100 nm | | | |
|---|---|---|---|---|
| | no NaCl | | +100 mM NaCl | |
| DNA/PLL | <100 nm | >100 nm | <100 nm | >100 nm |
| 0.43 | 72(50) | 28(200) | 36(28) | 64(280) |
| 0.65 | 68(42) | 32(196) | 36(63) | 64(304) |
| 0.88 | — | 100(10000) | — | 100(10000) |

TABLE 3-continued

The effect of varying the DNA/PLL charge (monomoer:monomer) ratio on the sizes of PLL/DNA complexes with the addition of 0.97 umol DTBP. The sizes were determined by quasi elastic light scattering and numbers indicate the percent of particles <100 nm or >100 nm. Number in parentheses indicate the size (diameter in nm) of the most abundant species within that size range.

| | Percentage of Particles Less or Greater Than 100 nm | | | |
|---|---|---|---|---|
| | no NaCl | | +100 mM NaCl | |
| DNA/PLL | <100 nm | >100 nm | <100 nm | >100 nm |
| 1.31 | — | 100(10000) | — | 100(10000) |
| 1.74 | 8(65) | 92(150,680) | 7(84) | 93(1000) |
| 2.61 | 69(33) | 31(118) | 11(91) | 89(836) |
| 4.12 | 96(43.4) | 4(6580) | — | 100(204,1152) |
| 6.18 | 100(22.4) | — | — | 100(222,1052) |
| 0.43 + DTBP | 29(55) | 71(331) | 43(31) | 57(131,374) |
| 0.65 + DTBP | 43(31) | 69(339) | 16(54) | 84(350) |
| 0.88 + DTBP | 13(72) | 87(431,1640) | 21(41) | 79(707,4690) |
| 1.31 + DTBP | 87(45,100) | 3(260) | — | 100(10000) |
| 1.74 + DTBP | 87(45,99) | 3(256) | 73(55) | 27(191) |
| 2.61 + DTBP | 100(32,98) | — | 77(51) | 23(130) |
| 4.12 + DTBP | 99(27.9) | 1(6468) | 69(67.6) | 31(142,2000) |
| 6.18 + DTBP | 94(35.2) | 6(6580) | 96(68) | 4(6813) |
| 4.12 + DTBP + DTT | | | — | 100(362,8800) |
| 6.18 + DTBP + DTT | | | — | 100(381,8755) |

In Table 3, it is clear, that PLL/DNA complexes with ratio higher then 1.3 became substantially less prone to aggregate in the presence of 100 mM NaCl after DTBP modification. The PLL/DNA complex stabilized reaction is intra complex crosslinking because the treatment of the modified PLL/DNA complexes with ratio 4.12 and 6.18 by 50 mM DTT for 1 h resulted in aggregation. In this condition the crosslinks should be cleaved but the level of lysine modification is not changed.

Effect of PLL/DTBP Ratio on the Size and Stability of PLL/DNA Complexes.

The PLL/DNA complex in ratio 4.12 was treated by different concentrations of DTBP during 2 h. The size of particles without and in presence of 100 mM NaCl was determined by quasi elastic light scattering.

TABLE 4

The effect of varying the DTBP/PLL ratio (molar ratio of DTBP to lysine residue) on the sizes of PLL/DNA complexes. The sizes were determined by quasi elastic light scattering and numbers indicate the percent of particles <100 nm or >100 nm. Number in parentheses indicate the size (diameter in nm) of the most abundant species within that size range.

| | Percentage of Particles Less or Greater Than 100 nm | | | |
|---|---|---|---|---|
| DTBP/PLL | no NaCl | | + 100 mM NaCl for 1 h | |
| Ratio | <100 nm | >100 nm | <100 nm | >100 nm |
| 0 | 75(88) | 25(586) | — | 100(7524) |
| 1.01 | 93(44) | 7(6874) | 37(92) | 63(600) |
| 2.03 | 95(35) | 5(550) | 75(66) | 25(190,4658) |
| 3.05 | 100(52) | — | 100(86) | — |

Table 4 shows that an excess of DTBP was needed for complex protection from salt dependent aggregation. It should be noted that DTBP up to ratio of 3.05 did not induce crosslinking between DNA/PLL particles. For samples with DTBP/PLL ratio 2.03 and 3.05 zeta potential were 16.16±3.23 mV and 20.33±3.3 mV respectively in 25 mM HEPES pH 8.0, 100 mM NaCl.

Stability of DNA/PLL Complexes to Disruption by Polyanion Dextran Sulfate (DS).

Figure 5:
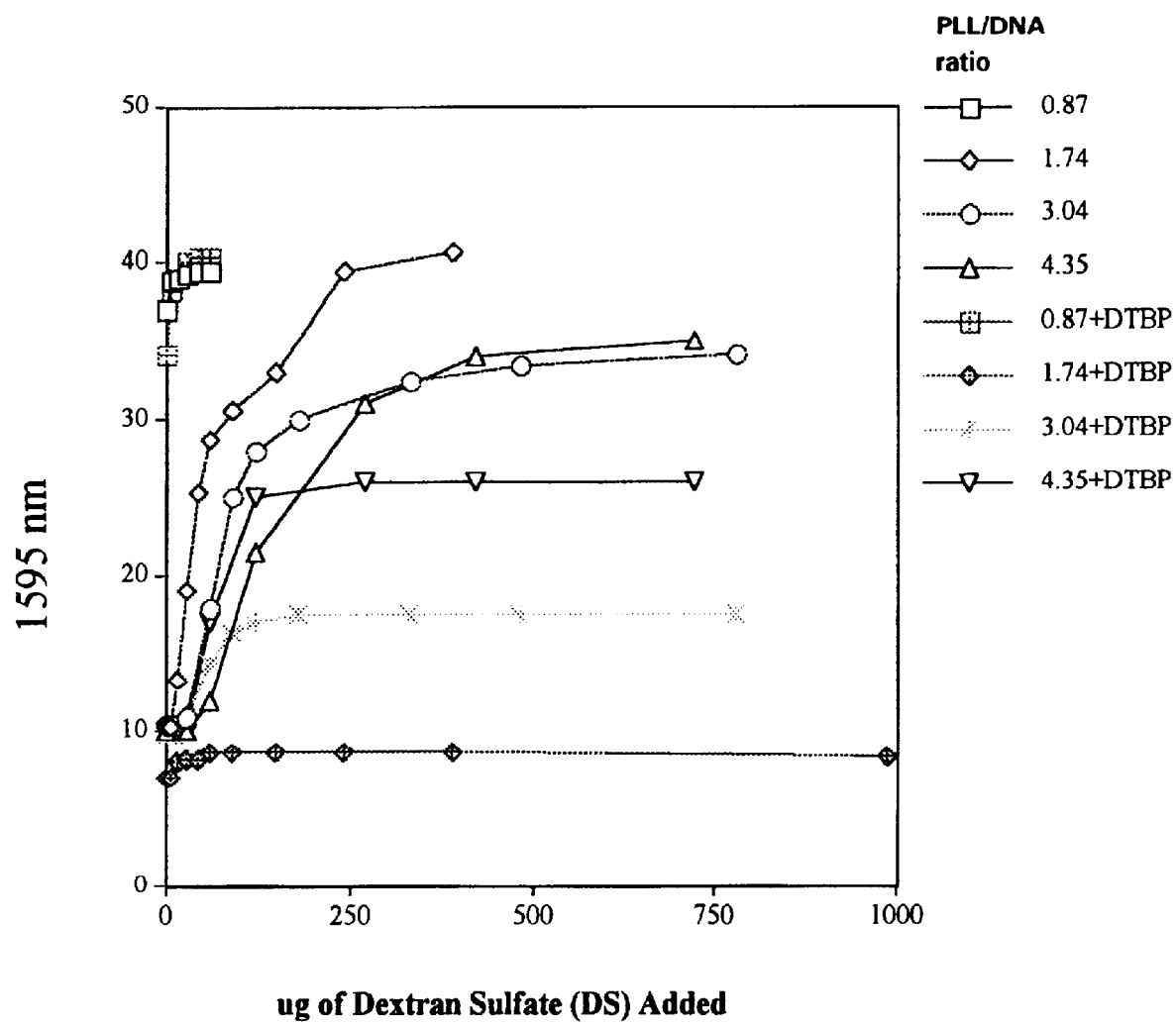
FIG. 5 illustrates the ability of dextran sulfate (DS) to enable ethidium bromide to interact with plasmid DNA that has been complexed with varying ratios of PLL/DNA (molar ratio of lysine residue to DNA base) (numbers in the legends) with or without the addition of DTBP.

DNA/PLL complexes (molar ratio of 0.87, 1.74, 3.04 or 4.35 as indicated in FIG. 5) were prepared as before but in 1 ml of buffer. 0.97 umol of DTBP were added. The mixtures were incubated 2 hours at room temperature. 10 ul of ethidium bromide (EB) (0.1 mg/ml) were added in every sample and the samples were incubated 30 min. The aliquot portions of DS were then added sequentially, with mixing. After each addition, the fluorescence was allowed to stabilize 30 seconds.

Addition of PLL to DNA in solution gave rapid falls in fluorescence, corresponding to complex formation. Addition of DS to pre-formed complexes can restore EB fluorescence and can be taken as indicator of complex stability (FIG. 5). Without DTBP, the EB fluorescence rose with the addition of DS in every ratio of PLL/DNA (FIG. 5). With DTBP, the increase was attenuated and there was a clear influence of DTBP modification on complex stability: the fraction of complexes could not be disrupted in any DS concentration. The part of complexes which are stable to disruption by DS depended on PLL/DNA ratio.

DNA/PAA Complexes.

Polyallylamine (PAA) is similar to PLL and contains primary amino groups. But average pK of PAA is low then PLL because stronger influence of one group to another.

TABLE 5

The effect of varying the DNA/PAA ratio on the sizes of PAA/DNA complexes with or without the addition of DTBP. The sizes were determined by quasi elastic light scattering and numbers indicate the percent of particles <100 nm or >100 nm. Number in parentheses indicate the size (diameter in nm) of the most abundant species within that size range.

| | Percentage of Particles Less or Greater Than 100 nm | | | |
|---|---|---|---|---|
| | no NaCl | | +NaCl | |
| PAA/DNA Ratio | <100 nm | >100 nm | <100 nm | >100 nm |
| 2.17 + DTBP | 7(106) | 77(455),16(4436) | — | 100(2064) |
| 4.34 + DTBP | 93(66) | 7(6900) | 70(94) | 30(916) |
| 6.51 + DTBP | 93(53) | 6(163) | 81(92) | 19(870) |
| 8.68 + DTBP | 97(55) | 3(5607) | 81(62) | 19(182) |
| 4.34 | 55(71) | 45(352) | 4(79) | 96(863) |

The results in Table 5 are very similar to the results with PLL/DNA complexes, but large excess of polycations are required for the preparation of stable small particles.

DNA/Histone H1 Complexes.

H1 has total positive charge 55 per molecule (Mw 21.3 kDa) and can form an inter polyelectrolyte complex with DNA. In contrast to PLL and PAA, interaction of Hi with DNA leads to considerable increase of turbidity in broad range of H1 concentration. The turbidity is not changed after addition of 100 mM NaCl. Treatment of H1/DNA complex with charge ratio 3.42 by DTBP leads to significant decrease of turbidity from 1929 to 348. Following addition of NaCl causes the turbidity to increase to 458.

Figure 6:
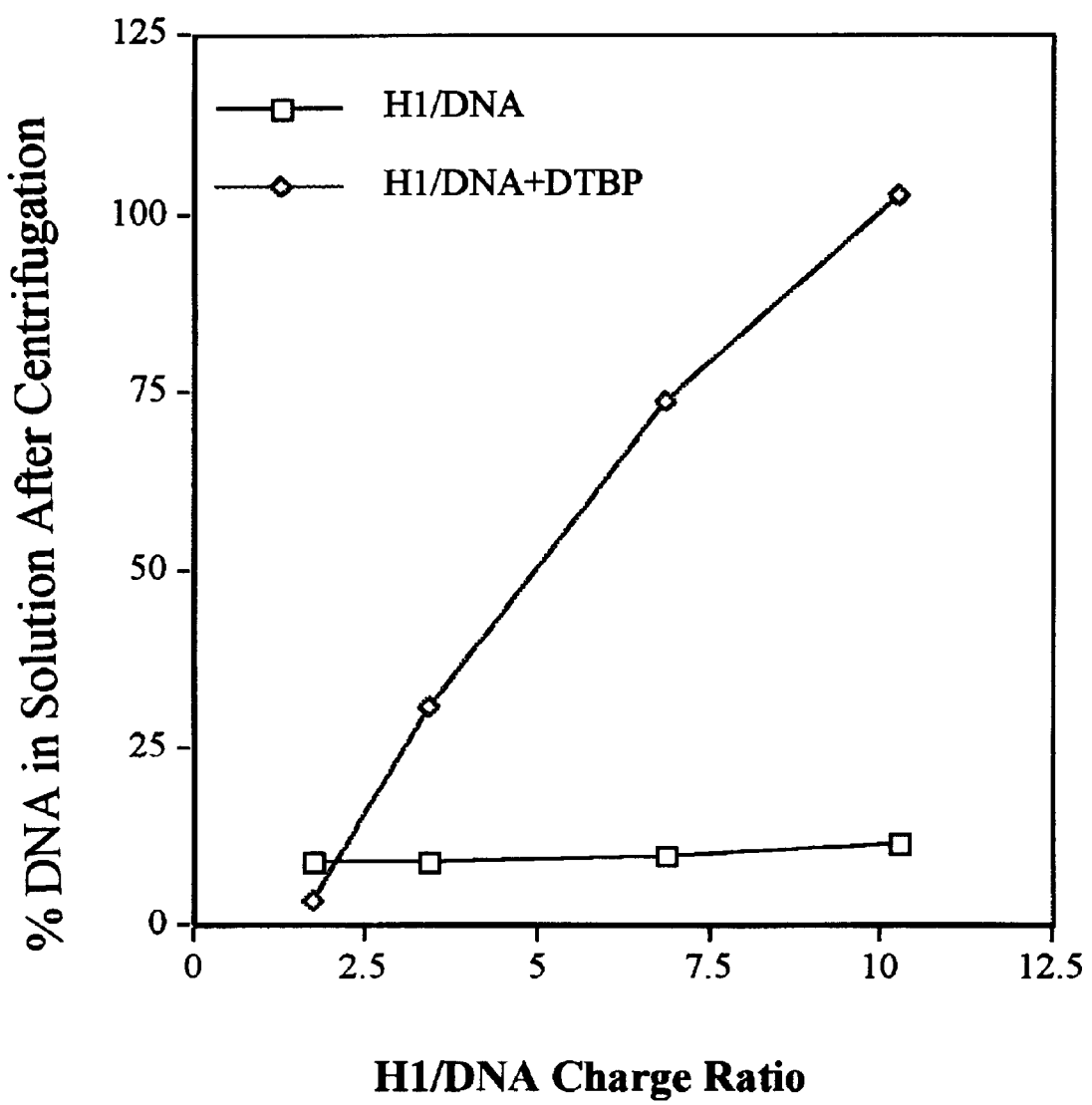
FIG. 6 illustrates the effect of varying the histone/DNA ratio on the sizes of histone/DNA complexes with the addition of DTBP.

The centrifugation of HI/DNA complexes in buffer with 100 mM NaCl 7 min at 12,000 rpm results in precipitation of DNA, but after DTBP modification most part of DNA stays in solution, which indicates presence of small particles (FIG. 6). Table 6 shows that the sizes of the particles formed with DTBP (Table 6B) in 100 mM NaCl were much smaller that the particle formed without DTBP (Table 6A).

Findings:
1. DNA template polymerization of large polymers yields small particles that do not aggregate in physiological salt solutions.
2. The ability to prepare small particles of condensed DNA that do not aggregate in a physiologic salt solution will be an extremely useful formulation for gene transfer and therapy.

EXAMPLE 9

Step DNA Template Polymerization Using the Comonomers of AEPD and a PEGylated-AEPD (Compound 18).

Step polymerization with DNA as a template was performed using the polyamine N,N'-bis(2-aminoethyl)-1,3-propanediamine (AEPD) as in Example 1 except pegylated AEPD (Compound 18, N2,N2,N3,N3-tetra(PEG-amino propyl)-AEPD, or will be referred to as AEPD-PEG) was added to the reaction mixture along with AEPD. This example teaches how to prepare non-aggregated, water-soluble particles (diameter <100 nm) of condensed DNA via the process of template polymerization.

Methods:

The mixture of the following amines was used as comonomers:
1. N,N'-bis(2-aminoethyl)-1,3-propanediamine (AEPD, Aldrich, Milwaukee, Wis.).
2. N2,N2,N3,N3-tetra(PEG-amino propyl)-AEPD (Compound 18).

The following crosslinker was used:
1. Dimethyl-3,3'-dithiobispropionimidate (DTBP, S-S cleavable bisimido ester, Pierce Chemical Co.).

Optimized reaction conditions with AEPD/AEPD-PEG mixture were as follows. Plasmid DNA (pCIluc, 10 ug), AEPD (58 ug), AEPD-PEG (5 mg) and DTBP (187 ug) were mixed in 0.5 ml of buffer solution (20 mM HEPES, 1 mM EGTA, pH 8.5). Molar ratio of total AEPD (AEPD+AEPD-PEG) to DNA base was 20:1. Reaction was allowed to proceed for three hours at room temperature. At 10, 30, 60 and 180 min time points particle sizing was performed using photon correlation spectrometer as described in Example 1.

TABLE 6

The effect of varying the H1DNA charge ratio on the sizes of PAA/DNA complexes without (A) or with (B) the addition of DTBP. The sizes were determined by quasi elastic light scattering and numbers indicate the percent of particles <100 nm or >100 nm. Number in parentheses indicate the size (diameter in nm) of the most abundant species within that size range.

| | Percentage of Particles Less or Greater Than 100 nm | | | |
|---|---|---|---|---|
| | −NaCl | | +NaCl | |
| Charge ratio(+/−) | <150 nm | >150 nm | <150 nm | >150 nm |
| A. H1/DNA - no DTBP | | | | |
| 1.55 | 7(44) | 29(377)64(1376) | 47(25) | 36(491) |
| 3.1 | 6(75) | 88(500)10(6000) | — | 92(470)8(8000) |
| 6.2 | — | 10(159)90(589) | — | 62(350)38(1825) |
| 9.3 | 9(113) | 91(348) | — | 2(208)98(1404) |
| B. H1/DNA + DTBP | | | | |
| 1.55 | 19(27)6(131) | 75(886) | — | 84(892)16(8000) |
| 3.1 | 28(37) | 12(168)60(603) | — | 28(171)72(512) |
| 6.2 | — | 75(166)25(1168) | 47(55) | 53(222) |
| 9.3 | 48(117) | 52(306) | 56(75) | 44(172) |

The data obtained was compared with the experiment where only AEPD was used as monomer. Three independent samples of each template polymerization reaction mixture were measured and the data was expressed as mean +/−SD. Transmission electron microscopy of the AEPD/AEPD-PEG mixture samples was performed as described in Example 1.

Results:

Formation of particles of condensed DNA for AEPD/AEPD-PEG template polymerization mixture was confirmed both by dynamic light scattering and by electron microscopy. Unlike AEPD alone 20:1 mixture which yields aggregates, AEPD/AEPD-PEG mixture resulted in increased population of non-aggregated individual DNA particles with the size <100 nm of characteristic rod morphology.

85% of the condensed DNA stays in solution after centrifugation in microcentrifuge for 5 min at 12000 g. At this conditions 100% of DNA condensed with AEPD alone (1:20 ratio) was found precipitated.

The 1:20 DNA/AEPD/DTBP reaction mixture in the presence of AEPD-PEG molecules with protected primary amino groups (precursor of AEPD-PEG monomer, see Example ??) resulted in formation of aggregated DNA.

Findings:
1. Template polymerization can be performed in the presence of pegylated AEPD molecules. PEG-containing monomer was included into final condensed DNA complex.
2. Addition of pegylated PEG into standard DNA/AEPD/DTBP template polymerization mixture resulted in formation of non-aggregated particles of condensed DNA via the mechanism of steric stabilization.

EXAMPLE 10
Chain Polymerization of Compound 11 on a DNA Template in an Organic Solvent.

Plasmid DNA (pCI luc, 10 mg) in 660 $\mu$L water was combined with 1380 $\mu$L methanol and 660 $\mu$L chloroform containing 144 mg of Compound 11, giving a clear solution with a 7 fold excess of positive charge. The solution was vortexed and allowed to stand at room temperature for 20 minutes. One half of the monophase was reserved. The remaining monophase was separated into two layers by the addition of an additional 375 $\mu$L water. The two resulting layers were separated. The presence of DNA in the chloroform layer was confirmed by absorbence at 260 nm. The sizes of the particles in the chloroform layer and in the reserved monophase were measured on a Brookhaven Zeta-Plus particle sizer. The Bligh/Dyer monophase (Bligh, E. G. and Dyer, W. J. (1959) A rapid method of total lipid extraction and purification. Can. J. Biochem. Physiol., 37, 911–917.) had two groups of particles in the size range of 80–128 nm and 7000–10000 nm. The chloroform layer showed one group of particles with a size range of 4–7 nm, however the signal intensity was low.

The Bligh/Dyer monophase and the chloroform layer were polymerized in the presence of 1% AIBN (Aldrich Chemical Company) for 1 hour at 55° C. Particle size was measured after the polymerization. The Bligh/Dyer monophase contained one population of particles with a size range of 700–1000 nm. The chloroform layer contained one population of particles with a size range of 340–400 nm. The polymerized reaction products were analyzed on a SDS-PAGE gel (Novex, 10–20% tricene). Approximately 50 $\mu$g of the polymerized reactions and a control consisting of 7 $\mu$g DNA and 50 $\mu$g compound 11 without polymerization were loaded onto the gel and visualized with coumassie staining. A smear of high-molecular weight polymer beginning in the well was observed in both of the polymerization reactions. The control exhibited one band of low molecular weight.

EXAMPLE 11

Methods:

Dextran sulfate (Mw=500 000, DS) was obtained from Sigma. Polymethacrylic acid sodium salt (PMAA, Mw=9 500) was obtained from Aldrich. Caged DNA particles were prepared as described in example "Template polymerization (caging) of large polymers" with DTBP as cross-linking agent. Zeta-potentials of the obtained particles were measured using Zeta-Plus Photon Correlation Spectrometer (Brookhaven Instruments Corp.). Ninety degree light scattering measurements and TOTO binding assay were performed using Fluorescence Spectrophotometer. TOTO assay was used to assess the degree of DNA condensation (Wong F M. Reimer D L. Bally M B, Cationic lipid binding to DNA: characterization of complex formation. Biochemistry. 35(18):5756–63, 1996).

Results:

After the obtaining soluble particles of positevly-charged caged DNA/PLL complexes their surface was rendered negatively charged by complexing it with the excess of polyanion. It was found that upon addition of polyanion solution to soluble DNA/PLL complex the net charge of the triple complex can be changed to the opposite at the certain concentration of the polyanion

TABLE 7

| DS added ug | Z-potential uncaged | Z-potential caged |
|---|---|---|
| 0 | 29.55 | 28.5 |
| 50 | 33.68 | 19.73 |
| 100 | −17.25 | −14.66 |
| 150 | −22.45 | −13.73 |
| 200 | −19.84 | −18.21 |
| 300 | | |
| 400 | | |
| 500 | −19.21 | −14.33 |

Table 7. Zeta potential of caged and non-caged DNA/PLL (1:6) complexes after addition of dextran-sulfate (DS). Complexes were prepared with 30 ug of DNA and 114 ug of PLL and caged with 240 ug of DTBP for 2 hrs.

Triple complexes formed at 150 ug of DS were tested on solubility at physiological salt. It was found that 60% of 190 stays in the solution after 5 min centrifugation at 12 000 g for both caged and uncaged complexes. Particle sizing using dynamic light scattering demonstrated 80% particles <150 nm in diameter at these conditions.

TABLE 8

| DS added, ug | TOTO signal, % of native DNA uncaged | TOTO signal % of native DNA caged |
|---|---|---|
| 0 | 4 | 3 |
| 50 | 3 | 2 |
| 100 | 14 | 7 |
| 200 | 49 | 27 |
| 300 | 43 | 22 |
| 400 | 39 | 20 |
| 500 | 38 | 20 |

Table 8. DNA condensation after complexing DNA/PLL complexes with dextran sulfate.

TOTO assay (Table. 8) demonstrated that DNA stays condensed after formation of negatively charged triple complex though some partial decondensation occured. Caged complex was found more resistant to decondensation during recharging (80% condensation preserved at 400–500 ug DS added).

It is possible to recharge DNA/PLL complexes with other polyanions. The similar data were obtained with polymethacrylic acid (not shown).

Syntheses of Compounds
Materials and Methods:

H-NMR spectra were recorded on a Bruker AC 250 or a Bruker AC 300 spectrophotometer with chemical shifts given in parts per million downfield from an internal standard of tetramethylsilane. Diamino-N-methyldipropylamine (Aldrich Chemical Co.), Boc anhydride (Aldrich Chemical Co.), triethylamine (Aldrich Chemical Co.), trifluoroacetic anhydride (Aldrich Chemical Co.), 9-bromo-1-nonanol (Aldrich Chemical Co.), acryloyl chloride (Aldrich Chemical Co.), 3-bromopropylamine hydrobromide (Aldrich Chemical Co.), 7-bromo-1-octene (Aldrich Chemical Co.), trimethylamine (25% solution in water) (Aldrich Chemical Co.), methyl iodide (Aldrich Chemical Co.), N,N,N'N'-tetramethyl-propane diamine (Aldrich Chemical Co.), N,N,N',N',N"-pentamethylethylentriamine (Aldrich Chemical Co.) were used as supplied. All solvents were obtained from Aldrich Chemical Co. All anhydrous solvents were obtained from Aldrich Chemical Co. in Sure/Seal__containers.

Compound 1

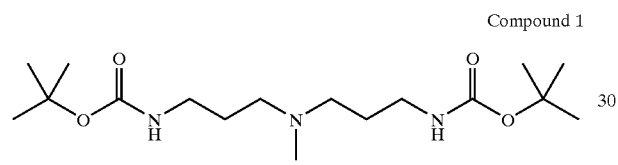

3,3'-(N',N"-tert-butoxycarbonyl)-N-methyldipropylamine (1). 3,3'-Diamino-N-methyldipropylamine (0.800 mL, 0.721 g, 5.0 mmol) was dissolved in 5.0 mL 2.2 N sodium hydroxide (11 mmol). To the solution was added Boc anhydride (2.50 mL, 2.38 g, 10.9 mmol) with magnetic stirring. The reaction mixture was allowed to stir at room temperature overnight (approximately 18 hours). The reaction mixture was made basic by adding additional 2.2 N NaOH until all t-butyl carboxylic acid was in solution. The solution was then extracted into chloroform (2×20 mL). The combined chloroform extracts were washed 2×10 mL water and dried over magnesium sulfate. Solvent removal yielded 1.01 g (61.7%) product as a white solid: $^1$H-NMR (CDCl$_3$) d 5.35 (bs, 2H), 3.17 (dt, 4H), 2.37 (t, 4H), 2.15 (s, 3H), 1.65 (tt, 4H), 1.45 (s, 18H).

Compound 2

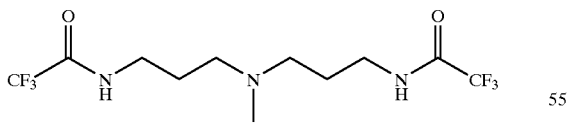

3,3'-Trifluoroacetamidyl-N-methyldipropylamine (2).
3,3'-Diamino-N-methyldipropylamine (0.504 mL, 436 mg, 3.0 mmol) and triethylamine (0.920 mL, 6.6 mmol) were dissolved in 20 mL dry methylene chloride. The solution was chilled on an ice bath. Trifluoroacetic anhydride (0.932 mL, 1.39 g, 6.6 mmol) dissolved in 40 ml dry methylene chloride was added dropwise with magnetic stirring over a period of approximately 20 minutes. The reaction was allowed to come to room temperature and to stir overnight (approximately 18 hours). The reaction mixture was washed 2×15 mL 2% sodium bicarbonate, 2×15 mL water, and dried over magnesium sulfate. Solvent removal yielded 763 mg (67.9%) product as a yellow oil: 1H-NMR (CDCl$_3$) d 8.20 (bs, 2H), 3.45 (dt, 2H), 2.47 (t, 2H), 2.20 (s, 3H), 1.75 (tt, 2H).

Compound 3

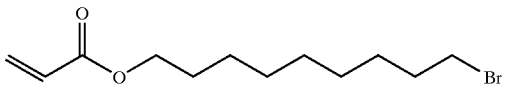

9-Bromononacrylate (3).
9-Bromo-1-nonanol (0.939 g, 4.0 mmol) was dissolved in 4.0 mL anhydrous diethyl ether in a flame dried 10 mL r.b. flask under dry nitrogen. Sodium carbonate (6.36 g, 6.0 mmol) was added to the reaction mixture. Acryloyl chloride (0.356 mL, 0.397 g, 4.2 mmol) dissolved in 3.5 mL anhydrous ether was added dropwise over a period of approximately 10 minutes. The reaction mixture was allowed to come to room temperature and stir for two days. The reaction mixture was diluted to 40 mL with ether and washed 3×10 mL 2% sodium bicarbonate to remove unreacted acryloyl chloride. The organic layer was dried over magnesium sulfate and passed through a short (approximately 7 g) alumina column to remove unreacted alcohol. Solvent removal yielded 390 mg (35.2%) product as a clear liquid: $^1$H-NMR (CDCl$_3$) d 6.40 (dd, 1H), 6.12 (dd, 1H), 5.82 (dd, 1H), 4.15 (t, 4H), 3.40 (t, 2H), 1.85 (dt, 2H), 1.65 (dt, 2H), 1.35 (m, 10H).

Compound 4

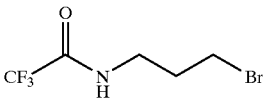

3-Bromo-1-(trifluoroacetamidyl)propane (4).
3-Bromopropylamine Hydrobromide (2.19 g, 10.0 mmol) and triethylamine (1.67 mL, 12.0 mmol) were dissolved in 60 mL dry methylene chloride. The solution was chilled on an ice bath. Trifluoroacetic anhydride (1.69 mL, 2.51 g, 12.0 mmol) dissolved in 60 mL dry methylene chloride was added dropwise over approximately 20 minutes. The reaction was allowed to come to room temperature and was stirred overnight (approximately 18 hours). The reaction mixture was washed 1×10 mL 2% sodium bicarbonate, 1×10 mL water, and dried over magnesium sulfate. Solvent removal yielded 2.07 g (88.5%) product as a white powder: $^1$H-NMR (CDCl$_3$) d 6.70 (bs, 1H), 3.55 (dt, 2H), 3.45 (t, 2H), 2.17 (tt, 2H).

Compound 5

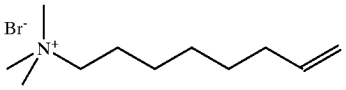

1-Octene-7-trimethylammonium Bromide (5).
7-Bromo-1-octene (0.168 mL, 191.2 mg, 1.00 mmol) was combined with trimethylamine (2.40 mL 25% solution in water). The mixture was incubated at 50 C__ on a rotary shaker for 18 hours. Solvent removal and recrystalization from acetone/diethyl ether yielded 191.6 mg (76.6%) product as white plates: $^1$H-NMR (CDCl$_3$) d 5.75 (m, 1H), 5.00 (m, 2H), 3.60 (m, 2H), 3.45 (s, 9H), 2.05 (m, 2H), 1.75 (m, 2H), 1.40 (m, 6H).

Compound 6

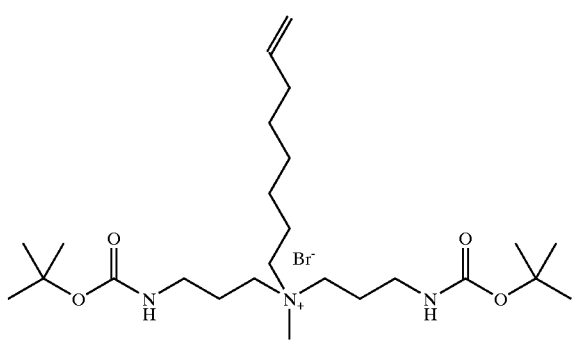

3,3'-(N',N"-tert-butoxycarbonyl)-N-(7-octene)-N-methyldipropyl-ammonium Bromide (6). Compound 1 (86.3 mg, 0.25 mmol) was combined with 7-bromo-1-octene and dissolved in 0.050 mL methyl sulfoxide. The reaction mixture was incubated at 55 C_for 18 hours. The viscous reaction mixture was triturated with ether twice. The remaining oil was recrystalized from chloroform/ether to yield 55.3 mg (48.7%) product as white crystals: $^1$H-NMR (CDCl$_3$) d 5.75 (m, 3H), 4.95 (m, 2H), 3.55 (m, 4H), 3.30 (m, 6H), 3.15 (s, 3H), 2.05 (m, 4H), 1.97 (m, 2H), 1.70 (m, 2H), 1.45 (s, 18H), 1.35 (m, 6H).

Compound 7

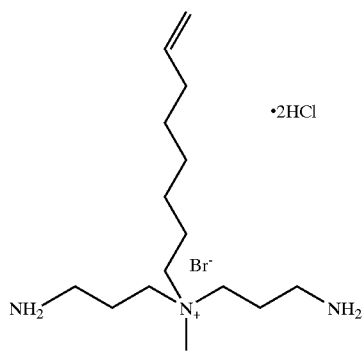

3,3'-diamine-N-(7-octene)-N-methyldipropylammonium Bromide (7).

Compound 6 was combined with 0.350 mL ethyl acetate, 0.150 mL methanol, and 0.150 mL 12 N hydrochloric acid. The reaction mixture was stirred at room temperature for 2.5 hours, during this time the reaction became homogenous. Solvent was removed and the product was precipitated from a small amount of methanol with ether to yield 36.0 mg (95.2%) product as a colorless oil: $^1$H-NMR (CD$_3$OD) d 5.85 (m, 1H), 5.00 (m, 2H), 3.55 (m, 4H), 3.45 (m, 2H), 3.20 (s, 3H), 3.15 (t, 4H), 2.25 (m, 4H), 2.10 (m, 2H) 1.85 (m, 2H), 1.50 (m, 6H).

Compound 8

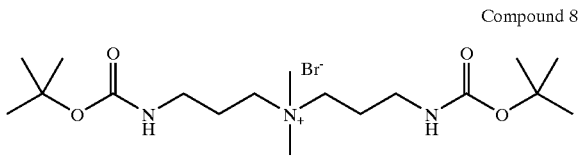

3,3'-(N',N"-tert-butoxycarbonyl)-N,N-dimethyldipropylammonium bromide (8). Compound 1(75.0 mg, 0.217 mmol) was dissolved in 0.5 mL dry ether, ethyl alcohol was added drop-wise until compound 1 was completely dissolved. The reaction solution was chilled on an ice bath and purged with dry nitrogen. Methyl iodide (0.021 mL, 33.7 mmol) was added, and the reaction mixture was stirred at 4 C_for 18 hours. Poured reaction mixture into water and washed with ether. After removal of water the product was dissolved in chloroform, decolorized with activated charcoal, and dried with magnesium sulfate. Solvent removal yielded 92.0 mg (87.0%) product as a yellow oil: $^1$H-NMR (CDCl$_3$) d 5.50 (bs, 2H), 3.60 (m, 4H), 3.30 (s, 6H), 3.25 (m, 4H), 2.07 (m, 4H), 1.45 (s, 18H).

Compound 9

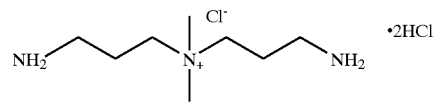

3,3'-Diamino-N,N-dimethyldipropylammonium Bromide (9).

Compound 8 (92.0 mg, 0.189 mmol) was dissolved in 0.200 mL ethyl acetate and 0.150 mL 12 N hydrochloric acid. The reaction mixture was stirred at room temperature for 1 hour. Solvent was removed and the oily residue was triturated three times with ether. The remaining product was dried in vacuo yielding 43.9 mg (100%) product as a yellow waxy solid: H-NMR (CD$_3$OD) d 3.55 (m, 4H), 3.20 (s, 6H), 3.20 (t, 4H), 2.22 (m, 4H).

Compound 10

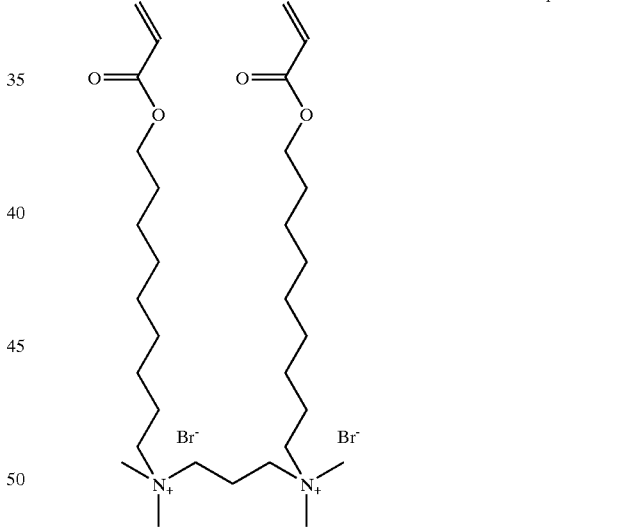

N,N'-Dinonacrylate-N,N,N',N'-tetramethylpropane-diammonium bromide (10).

N,N,N'N'-tetramethylpropane diamine (0.0252 mL, 0.15 mmol) and compound 3 (131 mg, 0.148 mmol) were dissolved in 0.150 mL dimethylformamide. The reaction mixture was incubated at 50 C_ for 5 days. The product was precipitated from the reaction mixture by the addition of ether. The resulting solid was collected and recrystalized twice from ethanol/ether yielding 56.9 mg (55.4%) product as white crystals: $^1$H-NMR (CDCl$_3$) d 6.40 (dd, 2H), 6.15 (dd, 2H), 5.85 (dd, 1H), 4.15 (t, 4H), 3.88 (m, 4H), 3.52 (m, 4H), 3.40 (s, 12H), 2.75 (m, 2H), 1.82 (m, 4H), 1.65 (m, 4H), 1.35 (m, 20H).

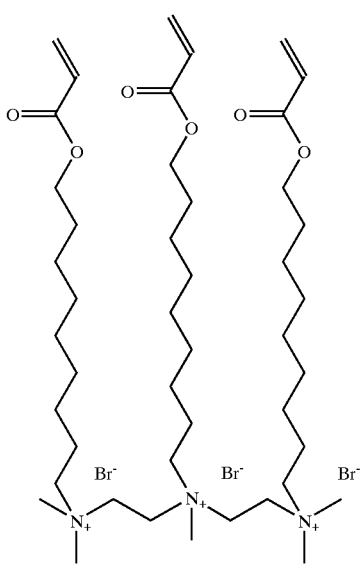

Compound 11

N,N',N''-Trinonacrylate-N,N,N',N',N''-pentamethyldiethylentriammonium Bromide (11). N,N,N',N',N''-pentamethylethylentriamine (0.031 mL, 0.15 mmol) and compound 3 (187 mg, 0.675 mmol) were dissolved in 0.150 mL dimethylformamide. The reaction mixture was incubated at 50 C__ for 5 days. The product was precipitated from the reaction mixture by the addition of ether. The resulting solid was collected and recrystalized from ethanol/ether yielding 36.6 mg (24.3%) product as white crystals: H-NMR (CDCl₃) d 6.40 (dd, 3H), 6.15 (dd, 3H), 5.83 (dd, 3H), 4.15 (t, 6H), 3.95 (m, 4H), 3.60 (m, 4H), 3.40 (s, 15H), 3.17 (m, 6H), 1.70 (m, 12H), 1.35 (m, 30H).

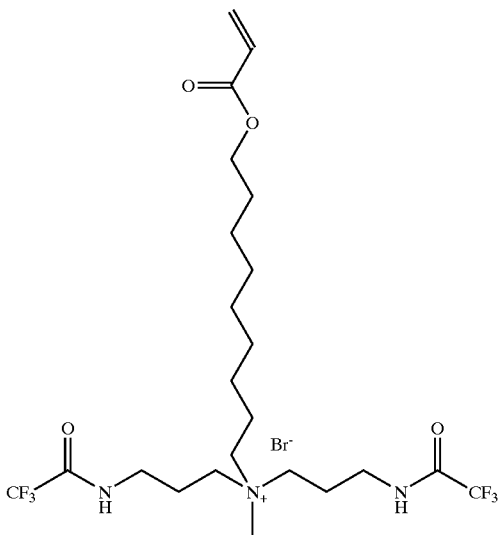

Compound 12

3,3'-Trifluoroacetamidyl-N-nonacrylate-N-methyldipropylammonium Bromide (12).

Compound 2 (233 mg, 0.691 mmol and compound 3 (282 mg, 1.01 mmol) were dissolved in 0.200 mL dimethylformamide. The reaction mixture was incubated at 50 C__for 4 days. The product was precipitated from the reaction mixture by the addition of ether. The resulting oil was triturated 3× with ether. The oil was dried in vacuo yielding 385.5 mg (90.8%) product as a clear oil: ¹H-NMR (CDCl₃) d 9.05 (bs, 2H), 6.35 (dd, 1H), 4.15 (t, 2H), 3.50 (m, 8H), 3.20 (m, 2H), 3.15 (s, 3H), 2.20 (m, 4H), 1.70 (m, 4H), 1.30 (m, 10H).

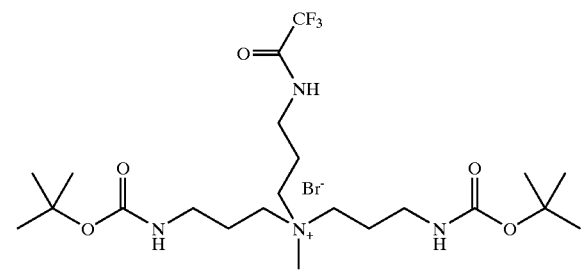

Compound 13

3,3'-(N',N''-tert-butoxycarbonyl)-N-(3'-trifluoroacetamidylpropane)-N-methyldipropylammonium bromide (13).

Compound 1 (100.6 mg, 0.291 mmol) and compound 4 (76.8 mg, 0.328 mmol) were dissolved in 0.150 mL dimethylformamide. The reaction mixture was incubated at 50 C__ for 3 days. TLC (reverse phase; acetonitrile: 50 mM ammonium acetate pH 4.0; 3:1) showed 1 major and 2 minor spots none of which corresponded to starting material. Recrystalization attempts were unsuccessful so product was precipitated from ethanol with ether yielding 165.5 mg (98.2%) product and minor impurities as a clear oil: ¹H-NMR (CDCl₃) d 9.12 (bs, 1H), 5.65 (bs, 2H), 3.50 (m, 8H), 3.20 (m, 4H), 3.15 (s, 3H), 2.20 (m, 2H), 2.00 (m, 4H), 1.45 (s, 18H).

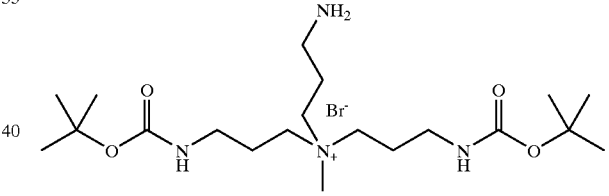

Compound 14

3,3'-(N',N''-tert-butoxycarbonyl)-N-(3''-aminopropane)-N-methyl-dipropylammonium bromide (14). Compound 13 (1.09 g, 1.88 mmol) was dissolved in mL methanol and 1.0 mL water. Sodium carbonate (1.00 g, 9.47 mmol) was added, and the reaction mixture was stirred at room temperature for 18 hours. Sodium carbonate and solvent were removed leaving a clear oil which was triturated 3× with ether. acuum drying yielded 898.2 mg (98.8%) product as a white solid. TLC (reverse phase; acetonitrile: 50 mM ammonium acetate pH 4.0; 1:3) gave 1 spot rf =0.54. ¹H-NMR (D20) d 3.55 (m, 6H), 3.27 (m, 4H), 3.05 (s, 3H), 2.87 (m, 2H), 1.97 (m, 6H), 1.45 (s, 18H).

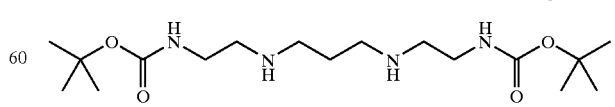

Compound 15

N₁,N₄-(tert-butoxycarbonyl)-bis(2-aminoethyl)-1,3-propanediamine (15)

AEPD (275 mg, 1.72 mmol) was dissolved in 5.0 mL tetrahydrofuran and chilled to 0° C. on an ice bath. BOC-ON (800 mg, 3.25 mmol, Aldrich Chemical Co.) dissolved in 3 mL tetrahydrofuran was added dropwise with magnetic stirring over approximately 15 minutes. The ice bath was removed and the stirring reaction mixture was allowed to come to room temperature. After 2 hours the solvent was removed on a rotary evaporator, and the residue was dissolved in 20 mL chloroform. The chloroform was washed with 2 N sodium hydroxide. The chloroform layer was then extracted with 0.1 N hydrochloric acid. The acid layer was then made basic by the addition of 2 N sodium hydroxide and the product was back extracted into chloroform. The chloroform was dried over magnesium sulfate. Solvent removal afforded 288 mg product (49.2%). $^1$H-NMR (CD$_3$OD) $\partial$ 3.15 (t, 4H), 2.65 (m, 8H), 1.70 (m, 2H), 1.45 (s, 18H).

Compound 16

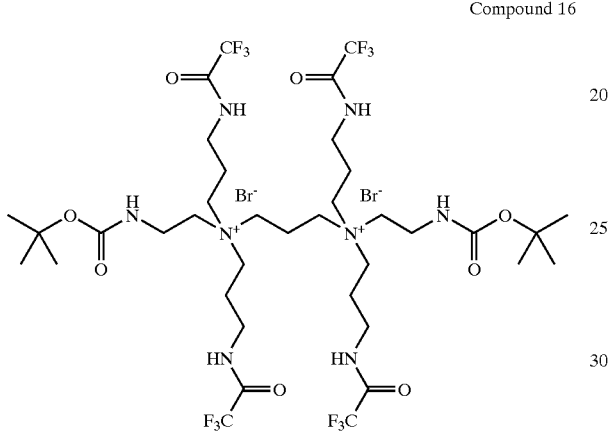

$N_2,N_2,N_3,N_3$-(3'-trifluoroacetamidylpropane)-$N_1,N_4$-(tert-butoxycarbonyl)-bis(2-aminoethyl)-1,3-propanediammonium Dibromide (16)

Compound 15 (33.0 mg, 91.7 μmol) and 3-Bromo-1-(trifluoroacetamidyl)propane (128 mg, 547 μmol) were combined in 200 μL dimethylformamide and incubated at 55° C. for 24 hours. TLC (silica: 90% acetonitrile, 10% 50 mM ammonium acetate pH 4.0) showed a mixture of products. Additional 3-Bromo-1-(trifluoroacetamidyl)propane (100 mg, 427 μmol) in 200 μL dimethylformamide and incubated an additional 24 hours. TLC showed 2 spots at rf of 0.51 and 0.58 in the above system when developed with dragendorffs reagent (Sigma Chemical Co.) Precipitation with diethyl ether yielded 56.0 mg product (53%). The final product may be a mixture of tri-alkylated AEPD and tetra-alkylated AEPD. Full characterization and purification is in progress.

Compound 17

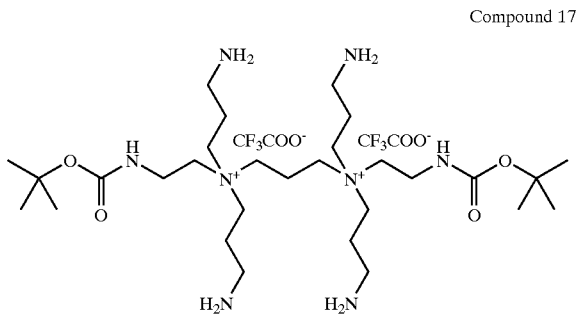

$N_2,N_2,N_3,N_3$-(3'-aminopropane)-$N_1,N_4$-(tert-butoxycarbonyl)-bis(2-aminoethyl)-1,3-propanediammonium di-trifluoroacetate (17)

Compound 16 (28.0 mg, 24.7 μmol) dissolved in 1 mL 6:4 methanol water along with calcium carbonate (104 mg, 1.0 mmol). The reaction mixture was stirred at 60° C. for 3 hours. TLC (silica: 90% acetonitrile, 10% 50 mM ammonium acetate pH 4.0) indicated completion of reaction with all material remaining at the origin. Product was isolated after removal of calcium carbonate by filtration to yield 13.0 mg (75.1%).

Compound 18

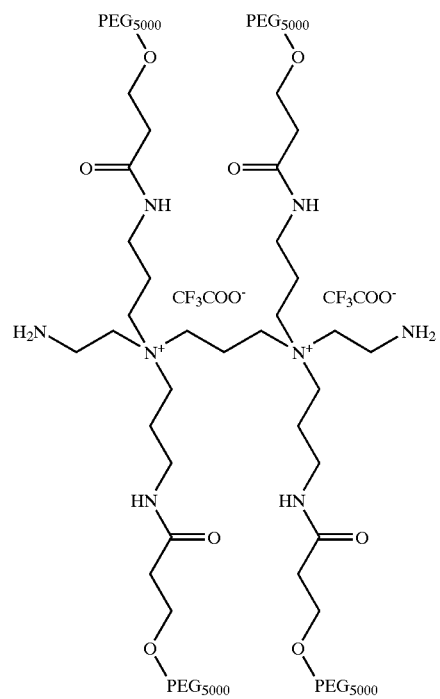

$N_2,N_2,N_3,N_3$-(3'-PEG$_{5000}$aminopropane)-$N_1,N_4$-bis(2-aminoethyl)-1,3-propanediammonium Di-trifluoroacetate (18)

Compound 17 (13 mg, 18.6 μmol) and 0-[2-(N-succinimidyloxycarbonyl)-ethyl]-O'-methylpolyethylene glycol 5,000 [NHS-Peg] (180 mg, 36 μmol) in 0.5 ML dimethylformamide. The reaction was stirred for 30 minutes. The reaction mixture was checked for the presence of primary amines by spotting on TLC plate and developing with ninhydrin spray. Primary amines were still present so additional NHS-Peg (80 mg, 16 μmol) was added. The reaction mixture was again screened for the presence of primary amines, none were found to be present. The reaction was stopped by precipitation with diethyl ether. The precipitate was washed 2× with diethyl ether, and dried under vacuum to yield 198 mg product. The product was dissolved in 2 mL trifluoroacetic acid, and incubated 20 minutes to remove the BOC protecting groups. The trifluoroacetic acid was removed under a stream of nitrogen. The residue was dried under vacuum to yield 198 mg product as an off-white solid. The presence of free amino groups after the removal of the BOC protecting groups was confirmed by a positive ninhydrin test. The final product should contain approximately 3 Peg chains per molecule as determined by the amount of NHS-Peg used in reaction.

The foregoing is considered as illustrative only of the principles of the invention. Furthermore, since numerous modifications and changes will readily occur to those skilled in the art, it is not desired to limit the invention to the exact construction and operation shown and described. Accordingly, all suitable modifications and equivalents fall within the scope of the invention.

We claim:

1. A monomer far forming a polymer having the structure

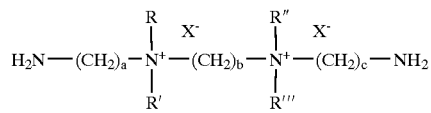

wherein,

R is selected from the group consisting of a steric stabilizer and hydrogen;

R' is selected from the group consisting of a steric stabilizer and hydrogen;

R" is selected from the group consisting of a steric stabilizer and hydrogen;

R'" is selected frown the group consisting of a steric stabilizer and hydrogen;

a is selected from the group consisting of 1–20;

b is selected from the group consisting of 1–20;

c is selected from the group consisting of 1–20; and,

X⁻ consists of a monovalent anion.

2. A monomer for forming a polymer having the stucture

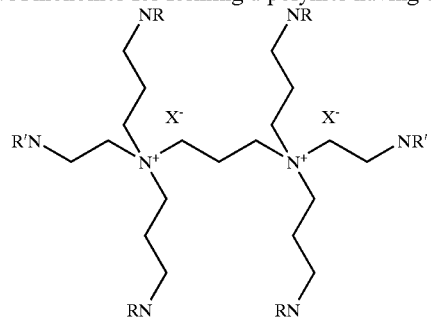

wherein,

R consists of a protecting group;

R' consists of an orthogonal protecting group; and,

X consists of monovalent anion.

3. A monomer for forming a polymer having the structure

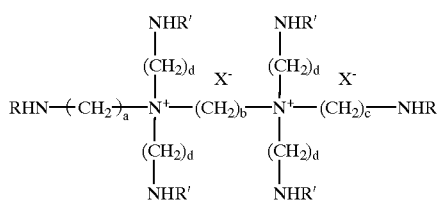

R is selected from the group consisting of orthogonal protecting groups, targeting groups, steric stabilizers, and hydrogen;

R' is selected from the group consisting of orthogonal protecting groups, targeting groups, steric molecules stabilizers, and hydrogen, a is selected from the group consisting of 1–20;

b is selected from the group consisting of 1–20;

c is selected from the group consisting of 1–20;

d is selected from the group consisting of 1–20; and

X–consists of a monovalent anion.

* * * * *